(12) United States Patent
Zingman

(10) Patent No.: US 8,136,712 B2
(45) Date of Patent: Mar. 20, 2012

(54) SURGICAL STAPLER WITH DISCRETE STAPLE HEIGHT ADJUSTMENT AND TACTILE FEEDBACK

(75) Inventor: Aron O. Zingman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 120 days.

(21) Appl. No.: 12/635,415

(22) Filed: Dec. 10, 2009

(65) Prior Publication Data
US 2011/0139852 A1 Jun. 16, 2011

(51) Int. Cl.
*A61B 17/04* (2006.01)
*A61B 17/10* (2006.01)

(52) U.S. Cl. .................... 227/179.1; 227/175.3
(58) Field of Classification Search ............. 227/179.1, 227/175.1–182.1, 110
See application file for complete search history.

(56) References Cited

U.S. PATENT DOCUMENTS

| | | | |
|---|---|---|---|
| 2,853,074 A | 9/1958 | Olson | |
| 3,551,987 A | 1/1971 | Wilkinson | |
| 4,304,236 A | 12/1981 | Conta et al. | |
| 4,429,695 A | 2/1984 | Green | |
| 4,473,077 A * | 9/1984 | Noiles et al. | 227/179.1 |
| 4,506,671 A | 3/1985 | Green | |
| 4,619,262 A | 10/1986 | Taylor | |
| 4,809,695 A | 3/1989 | Gwathmey et al. | |
| 4,844,068 A | 7/1989 | Arata et al. | |
| 5,104,025 A | 4/1992 | Main et al. | |
| 5,205,459 A * | 4/1993 | Brinkerhoff et al. | 227/179.1 |
| 5,222,945 A | 6/1993 | Basnight | |
| 5,285,945 A | 2/1994 | Brinkerhoff et al. | |
| 5,309,927 A | 5/1994 | Welch | |
| 5,405,072 A | 4/1995 | Zlock et al. | |
| 5,413,272 A | 5/1995 | Green et al. | |
| 5,415,334 A | 5/1995 | Williamson, IV et al. | |
| 5,417,361 A | 5/1995 | Williamson, IV | |
| 5,480,089 A | 1/1996 | Blewett | |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Rinaldi Rada
*Assistant Examiner* — Robert Long

(57) ABSTRACT

In various embodiments, a surgical stapler is provided that may comprise a body, a stapling head operably coupled to the body, an anvil movably supported relative to the stapling head for selective travel toward and away from the stapling head, and an anvil adjustment shaft supported by the body for selectively adjusting a position of the anvil relative to the stapling head. The adjustment shaft and/or the body may be configured to establish at least one predetermined staple forming height between the anvil and the stapling head irrespective of adjustment shaft rotation. Additionally, the adjustment shaft and/or the body may be configured to provide tactile feedback to a user rotating the anvil adjustment shaft, thereby providing the user of an indication of when an appropriate staple forming height has been reached. Various integrations of components described herein may also reduce the part count required for a surgical stapler, thereby reducing assembly time and manufacturing cost.

32 Claims, 16 Drawing Sheets

U.S. PATENT DOCUMENTS

| | | | |
|---|---|---|---|
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,505,363 A | 4/1996 | Green et al. | |
| 5,509,596 A | 4/1996 | Green et al. | |
| 5,529,235 A | 6/1996 | Boiarski et al. | |
| 5,533,661 A * | 7/1996 | Main et al. | 227/176.1 |
| 5,535,934 A | 7/1996 | Boiarski et al. | |
| 5,540,375 A | 7/1996 | Bolanos et al. | |
| 5,542,594 A | 8/1996 | McKean et al. | |
| 5,553,765 A | 9/1996 | Knodel et al. | |
| 5,560,530 A | 10/1996 | Bolanos et al. | |
| 5,560,532 A | 10/1996 | DeFonzo et al. | |
| 5,562,241 A | 10/1996 | Knodel et al. | |
| 5,564,615 A | 10/1996 | Bishop et al. | |
| 5,577,654 A | 11/1996 | Bishop | |
| 5,580,067 A | 12/1996 | Hamblin et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,628,446 A * | 5/1997 | Geiste et al. | 227/175.1 |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,780 A | 6/1997 | Green et al. | |
| 5,639,008 A | 6/1997 | Gallagher et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,685,474 A | 11/1997 | Seeber | |
| 5,690,269 A | 11/1997 | Bolanos et al. | |
| 5,692,668 A | 12/1997 | Schulze et al. | |
| 5,697,543 A | 12/1997 | Burdorff | |
| 5,704,534 A | 1/1998 | Huitema et al. | |
| 5,711,472 A | 1/1998 | Bryan | |
| 5,713,505 A | 2/1998 | Huitema | |
| 5,715,987 A | 2/1998 | Kelley et al. | |
| 5,718,360 A | 2/1998 | Green et al. | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,397 A | 7/1998 | Koukline | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,820,009 A | 10/1998 | Melling et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,871,135 A | 2/1999 | Williamson IV et al. | |
| 5,901,895 A | 5/1999 | Heaton et al. | |
| 5,911,353 A | 6/1999 | Bolanos et al. | |
| 5,915,616 A * | 6/1999 | Viola et al. | 227/179.1 |
| 5,941,442 A | 8/1999 | Geiste et al. | |
| 5,954,259 A | 9/1999 | Viola et al. | |
| 6,010,054 A | 1/2000 | Johnson et al. | |
| 6,032,849 A | 3/2000 | Mastri et al. | |
| 6,102,271 A | 8/2000 | Longo et al. | |
| 6,119,913 A | 9/2000 | Adams et al. | |
| 6,126,058 A | 10/2000 | Adams et al. | |
| 6,193,129 B1 | 2/2001 | Bittner et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,330,965 B1 | 12/2001 | Milliman et al. | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,505,768 B2 | 1/2003 | Whitman | |
| 6,578,751 B2 | 6/2003 | Hartwick | |
| 6,588,643 B2 | 7/2003 | Bolduc et al. | |
| 6,601,749 B2 | 8/2003 | Sullivan et al. | |
| 6,619,529 B2 | 9/2003 | Green et al. | |
| 6,629,630 B2 | 10/2003 | Adams | |
| 6,644,532 B2 | 11/2003 | Green et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,755,338 B2 | 6/2004 | Hahnen et al. | |
| 6,769,594 B2 | 8/2004 | Orban, III | |
| 6,786,382 B1 | 9/2004 | Hoffman | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,830,174 B2 | 12/2004 | Hillstead et al. | |
| 6,843,403 B2 | 1/2005 | Whitman | |
| RE38,708 E | 3/2005 | Bolanos et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,986,451 B1 | 1/2006 | Mastri et al. | |
| 6,988,650 B2 | 1/2006 | Schwemberger et al. | |
| 7,000,818 B2 | 2/2006 | Shelton, IV et al. | |
| 7,000,819 B2 | 2/2006 | Swayze et al. | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,070,083 B2 | 7/2006 | Jankowski | |
| 7,080,769 B2 | 7/2006 | Vresh et al. | |
| 7,083,075 B2 | 8/2006 | Swayze et al. | |
| 7,111,769 B2 | 9/2006 | Wales et al. | |
| 7,114,642 B2 | 10/2006 | Whitman | |
| 7,121,446 B2 | 10/2006 | Arad et al. | |
| 7,128,253 B2 | 10/2006 | Mastri et al. | |
| 7,128,254 B2 | 10/2006 | Shelton, IV et al. | |
| 7,140,527 B2 | 11/2006 | Ehrenfels et al. | |
| 7,143,926 B2 | 12/2006 | Shelton, IV et al. | |

| | | | |
|---|---|---|---|
| 7,147,138 B2 | 12/2006 | Shelton, IV | |
| 7,159,750 B2 | 1/2007 | Racenet et al. | |
| 7,168,604 B2 | 1/2007 | Milliman et al. | |
| 7,188,758 B2 | 3/2007 | Viola et al. | |
| 7,207,471 B2 | 4/2007 | Heinrich et al. | |
| 7,207,472 B2 | 4/2007 | Wukusick et al. | |
| 7,210,609 B2 | 5/2007 | Leiboff et | |
| 7,213,736 B2 | 5/2007 | Wales et al. | |
| 7,225,964 B2 | 6/2007 | Mastri et al. | |
| 7,234,624 B2 | 6/2007 | Gresham et al. | |
| 7,237,708 B1 | 7/2007 | Guy et al. | |
| 7,246,734 B2 | 7/2007 | Shelton, IV | |
| 7,258,262 B2 | 8/2007 | Mastri et al. | |
| 7,278,562 B2 | 10/2007 | Mastri et al. | |
| 7,278,563 B1 | 10/2007 | Green | |
| 7,296,724 B2 | 11/2007 | Green et al. | |
| 7,303,106 B2 | 12/2007 | Milliman et al. | |
| 7,303,107 B2 | 12/2007 | Milliman et al. | |
| 7,303,108 B2 | 12/2007 | Shelton, IV | |
| 7,328,828 B2 | 2/2008 | Ortiz et al. | |
| 7,328,829 B2 | 2/2008 | Arad et al. | |
| 7,354,447 B2 | 4/2008 | Shelton, IV et al. | |
| 7,364,060 B2 * | 4/2008 | Milliman | 227/175.1 |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,398,907 B2 | 7/2008 | Racenet et al. | |
| 7,398,908 B2 | 7/2008 | Holsten et al. | |
| 7,404,508 B2 | 7/2008 | Smith et al. | |
| 7,404,509 B2 | 7/2008 | Ortiz et al. | |
| 7,407,075 B2 | 8/2008 | Holsten et al. | |
| 7,407,078 B2 | 8/2008 | Shelton, IV et al. | |
| 7,410,086 B2 | 8/2008 | Ortiz et al. | |
| 7,416,101 B2 | 8/2008 | Shelton, IV et al. | |
| 7,419,080 B2 | 9/2008 | Smith et al. | |
| 7,422,136 B1 | 9/2008 | Marczyk | |
| 7,422,139 B2 | 9/2008 | Shelton, IV et al. | |
| 7,424,965 B2 | 9/2008 | Racenet et al. | |
| 7,431,188 B1 | 10/2008 | Marczyk | |
| 7,431,189 B2 | 10/2008 | Shelton, IV et al. | |
| 7,434,717 B2 | 10/2008 | Shelton, IV et al. | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,455,208 B2 | 11/2008 | Wales et al. | |
| 7,464,846 B2 | 12/2008 | Shelton, IV et al. | |
| 7,464,849 B2 | 12/2008 | Shelton, IV et al. | |
| 7,467,740 B2 | 12/2008 | Shelton, IV et al. | |
| 7,472,815 B2 | 1/2009 | Shelton, IV et al. | |
| 7,481,347 B2 | 1/2009 | Roy | |
| 7,481,349 B2 | 1/2009 | Holsten et al. | |
| 7,490,749 B2 | 2/2009 | Schall et al. | |
| 7,494,039 B2 | 2/2009 | Racenet et al. | |
| 7,500,979 B2 | 3/2009 | Hueil et al. | |
| 7,506,790 B2 | 3/2009 | Shelton, IV | |
| 7,506,791 B2 | 3/2009 | Omaits et al. | |
| 7,510,107 B2 | 3/2009 | Timm et al. | |
| 7,546,940 B2 | 6/2009 | Milliman et al. | |
| 7,549,564 B2 | 6/2009 | Boudreaux | |
| 7,556,186 B2 * | 7/2009 | Milliman | 227/182.1 |
| 7,559,450 B2 | 7/2009 | Wales et al. | |
| 7,568,603 B2 | 8/2009 | Shelton, IV et al. | |
| 7,575,144 B2 | 8/2009 | Ortiz et al. | |
| 7,588,175 B2 | 9/2009 | Timm et al. | |
| 7,588,176 B2 | 9/2009 | Timm et al. | |
| 7,597,229 B2 | 10/2009 | Boudreaux et al. | |
| 7,604,150 B2 | 10/2009 | Boudreaux | |
| 7,604,151 B2 | 10/2009 | Hess et al. | |
| 7,607,557 B2 | 10/2009 | Shelton, IV et al. | |
| 7,631,793 B2 | 12/2009 | Rethy et al. | |
| 7,644,848 B2 | 1/2010 | Swayze et al. | |
| 7,658,311 B2 | 2/2010 | Boudreaux | |
| 7,665,646 B2 | 2/2010 | Prommersberger | |
| 7,665,647 B2 | 2/2010 | Shelton, IV et al. | |
| 7,669,746 B2 | 3/2010 | Shelton, IV | |
| 7,669,747 B2 | 3/2010 | Weisenburgh, II et al. | |
| 7,670,334 B2 | 3/2010 | Hueil et al. | |
| 7,673,780 B2 | 3/2010 | Shelton, IV et al. | |
| 7,673,781 B2 | 3/2010 | Swayze et al. | |
| 7,673,782 B2 | 3/2010 | Hess et al. | |
| 7,673,783 B2 | 3/2010 | Morgan et al. | |
| 7,699,204 B2 | 4/2010 | Viola | |
| 7,717,312 B2 | 5/2010 | Beetel | |
| 7,721,930 B2 | 5/2010 | McKenna et al. | |
| 7,721,931 B2 | 5/2010 | Shelton, IV et al. | |
| 7,721,934 B2 | 5/2010 | Shelton, IV et al. | |
| 7,721,936 B2 | 5/2010 | Shalton, IV et al. | |
| 7,726,537 B2 | 6/2010 | Olson et al. | |
| 7,726,538 B2 | 6/2010 | Holsten et al. | |
| 7,731,072 B2 | 6/2010 | Timm et al. | |
| 7,735,703 B2 | 6/2010 | Morgan et al. | |
| 7,738,971 B2 | 6/2010 | Swayze et al. | |
| 7,740,159 B2 | 6/2010 | Shelton, IV et al. | |
| 7,743,960 B2 | 6/2010 | Whitman et al. | |
| 7,753,245 B2 | 7/2010 | Boudreaux et al. | |
| 7,753,904 B2 | 7/2010 | Shelton, IV et al. | |
| 7,766,209 B2 | 8/2010 | Baxter, III et al. | |
| 7,766,210 B2 | 8/2010 | Shelton, IV et al. | |
| 7,770,775 B2 | 8/2010 | Shelton, IV et al. | |
| 7,780,054 B2 | 8/2010 | Wales | |
| 7,784,662 B2 | 8/2010 | Wales et al. | |
| 7,793,812 B2 | 9/2010 | Moore et al. | |
| 7,794,475 B2 | 9/2010 | Hess et al. | |
| 7,798,386 B2 | 9/2010 | Schall et al. | |
| 7,799,039 B2 | 9/2010 | Shelton, IV et al. | |
| 7,810,692 B2 | 10/2010 | Hall et al. | |
| 7,810,693 B2 | 10/2010 | Broehl et al. | |
| 7,819,296 B2 | 10/2010 | Hueil et al. | |
| 7,819,297 B2 | 10/2010 | Doll et al. | |
| 7,819,298 B2 | 10/2010 | Hall et al. | |
| 7,819,299 B2 | 10/2010 | Shelton, IV et al. | |
| 7,832,408 B2 | 11/2010 | Shelton, IV et al. | |
| 7,832,611 B2 | 11/2010 | Boyden et al. | |
| 7,832,612 B2 | 11/2010 | Baxter, III et al. | |
| 7,837,080 B2 | 11/2010 | Schwemberger | |
| 7,845,533 B2 | 12/2010 | Marczyk et al. | |
| 7,845,537 B2 | 12/2010 | Shelton, IV et al. | |
| 7,857,185 B2 | 12/2010 | Swayze et al. | |
| 7,857,186 B2 | 12/2010 | Baxter, III et al. | |
| 7,861,906 B2 | 1/2011 | Doll et al. | |
| 7,866,527 B2 | 1/2011 | Hall et al. | |
| 7,922,063 B2 | 4/2011 | Zemlok et al. | |
| 2002/0117534 A1 | 8/2002 | Green et al. | |
| 2004/0094597 A1 | 5/2004 | Whitman et al. | |
| 2004/0108357 A1 | 6/2004 | Milliman et al. | |
| 2004/0164123 A1 | 8/2004 | Racenet et al. | |
| 2004/0173659 A1 | 9/2004 | Green et al. | |
| 2004/0222268 A1 | 11/2004 | Bilotti et al. | |
| 2004/0232201 A1 | 11/2004 | Wenchell et al. | |
| 2005/0103819 A1 | 5/2005 | Racenet et al. | |
| 2005/0184121 A1 | 8/2005 | Heinrich | |
| 2005/0189397 A1 | 9/2005 | Jankowski | |
| 2005/0263563 A1 | 12/2005 | Racenet et al. | |
| 2005/0274768 A1 | 12/2005 | Cummins et al. | |
| 2006/0011699 A1 | 1/2006 | Olson et al. | |
| 2006/0049229 A1 | 3/2006 | Milliman et al. | |
| 2006/0108393 A1 | 5/2006 | Heinrich et al. | |
| 2006/0180634 A1 | 8/2006 | Shelton IV et al. | |
| 2006/0226196 A1 | 10/2006 | Huell et al. | |
| 2006/0278680 A1 | 12/2006 | Viola et al. | |
| 2006/0278681 A1 | 12/2006 | Viola et al. | |
| 2006/0289602 A1 | 12/2006 | Wales et al. | |
| 2007/0023476 A1 | 2/2007 | Whitman et al. | |
| 2007/0023477 A1 | 2/2007 | Whitman et al. | |
| 2007/0034668 A1 | 2/2007 | Holsten et al. | |
| 2007/0084897 A1 | 4/2007 | Shelton, IV et al. | |
| 2007/0102472 A1 | 5/2007 | Shelton, IV | |
| 2007/0106317 A1 | 5/2007 | Shelton, IV et al. | |
| 2007/0114261 A1 | 5/2007 | Ortiz et al. | |
| 2007/0170225 A1 | 7/2007 | Shelton, IV et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175953 A1 | 8/2007 | Shelton, IV et al. | |
| 2007/0175955 A1 | 8/2007 | Shelton, IV et al. | |
| 2007/0181632 A1 | 8/2007 | Milliman | |
| 2007/0194079 A1 | 8/2007 | Hueil et al. | |

| Publication No. | Date | Inventor |
|---|---|---|
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096435 A1 | 4/2010 | Fuchs et al. |
| 2010/0108741 A1* | 5/2010 | Hessler et al. ............ 227/179.1 |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Schieb et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0001036 A1 | 1/2011 | Marczyk et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1* | 5/2011 | Milliman .................. 227/175.1 |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |

| | | | |
|---|---|---|---|
| 2011/0155781 A1 | 6/2011 | Swensgard et al. | |
| 2011/0155785 A1 | 6/2011 | Laurent et al. | |
| 2011/0155787 A1 | 6/2011 | Baxter, III et al. | |
| 2011/0163147 A1 | 7/2011 | Laurent et al. | |
| 2011/0174860 A1 | 7/2011 | Shelton, IV et al. | |
| 2011/0174863 A1 | 7/2011 | Shelton, IV et al. | |
| 2011/0192882 A1 | 8/2011 | Hess et al. | |

FOREIGN PATENT DOCUMENTS

| | | |
|---|---|---|
| CA | 2512960 A1 | 1/2006 |
| CA | 2514274 A1 | 1/2006 |
| CN | 1915180 A | 2/2007 |
| DE | 273689 C | 5/1914 |
| DE | 1775926 A | 1/1972 |
| DE | 3210466 A1 | 9/1983 |
| DE | 9412228 U | 9/1994 |
| DE | 19509116 A1 | 9/1996 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |

| | | | | | | |
|---|---|---|---|---|---|---|
| EP | 1344498 | B1 | 11/2005 | GB | 2425903 A | 11/2006 |
| EP | 1330989 | B1 | 12/2005 | JP | 6007357 A | 1/1994 |
| EP | 0771176 | B2 | 1/2006 | JP | 7051273 A | 2/1995 |
| EP | 1621138 | A2 | 2/2006 | JP | 8033641 A | 2/1996 |
| EP | 1621139 | A2 | 2/2006 | JP | 8229050 A | 9/1996 |
| EP | 1621141 | A2 | 2/2006 | JP | 2000033071 A | 2/2000 |
| EP | 1621145 | A2 | 2/2006 | JP | 2000171730 A | 6/2000 |
| EP | 1621151 | A2 | 2/2006 | JP | 2000287987 A | 10/2000 |
| EP | 1034746 | B1 | 3/2006 | JP | 2000325303 A | 11/2000 |
| EP | 1632191 | A2 | 3/2006 | JP | 2001286477 A | 10/2001 |
| EP | 1065981 | B1 | 5/2006 | JP | 2002143078 A | 5/2002 |
| EP | 1082944 | B1 | 5/2006 | JP | 2002369820 A | 12/2002 |
| EP | 1652481 | A2 | 5/2006 | JP | 2005505322 T | 2/2005 |
| EP | 1382303 | B1 | 6/2006 | JP | 2005103293 A | 4/2005 |
| EP | 1253866 | B1 | 7/2006 | JP | 2005131163 A | 5/2005 |
| EP | 1032318 | B1 | 8/2006 | JP | 2005131164 A | 5/2005 |
| EP | 1045672 | B1 | 8/2006 | JP | 2005131173 A | 5/2005 |
| EP | 1617768 | B1 | 8/2006 | JP | 2005131211 A | 5/2005 |
| EP | 1693015 | A2 | 8/2006 | JP | 2005131212 A | 5/2005 |
| EP | 1400214 | B1 | 9/2006 | JP | 2005137423 A | 6/2005 |
| EP | 1702567 | A2 | 9/2006 | JP | 2005152416 A | 6/2005 |
| EP | 1129665 | B1 | 11/2006 | JP | 2006-281405 A | 10/2006 |
| EP | 1400206 | B1 | 11/2006 | RU | 2187249 C2 | 8/2002 |
| EP | 1256317 | B1 | 12/2006 | RU | 2225170 C2 | 3/2004 |
| EP | 1728473 | A1 | 12/2006 | SU | 189517 A | 1/1967 |
| EP | 1728475 | A2 | 12/2006 | SU | 328636 A | 9/1972 |
| EP | 1479346 | B1 | 1/2007 | SU | 886900 A1 | 12/1981 |
| EP | 1484024 | B1 | 1/2007 | SU | 1333319 A2 | 8/1987 |
| EP | 1754445 | A2 | 2/2007 | SU | 1377053 A1 | 2/1988 |
| EP | 1759812 | A1 | 3/2007 | SU | 1561964 A1 | 5/1990 |
| EP | 1767163 | A1 | 3/2007 | SU | 1722476 A1 | 3/1992 |
| EP | 1769756 | A1 | 4/2007 | WO | WO 91/15157 A1 | 10/1991 |
| EP | 1769758 | A1 | 4/2007 | WO | WO 92/21300 A1 | 12/1992 |
| EP | 1581128 | B1 | 5/2007 | WO | WO 93/08755 A1 | 5/1993 |
| EP | 1785097 | A2 | 5/2007 | WO | WO 93/13718 A1 | 7/1993 |
| EP | 1790293 | A2 | 5/2007 | WO | WO 93/14690 A1 | 8/1993 |
| EP | 1800610 | A1 | 6/2007 | WO | WO 93/15850 A1 | 8/1993 |
| EP | 1300117 | B1 | 8/2007 | WO | WO 93/19681 A1 | 10/1993 |
| EP | 1813199 | A1 | 8/2007 | WO | WO 94/00060 A1 | 1/1994 |
| EP | 1813201 | A1 | 8/2007 | WO | WO 94/11057 A1 | 5/1994 |
| EP | 1813203 | A2 | 8/2007 | WO | WO 94/12108 A1 | 6/1994 |
| EP | 1813207 | A1 | 8/2007 | WO | WO 94/18893 A1 | 9/1994 |
| EP | 1813209 | A1 | 8/2007 | WO | WO 94/22378 A1 | 10/1994 |
| EP | 1487359 | B1 | 10/2007 | WO | WO 94/23659 A1 | 10/1994 |
| EP | 1599146 | B1 | 10/2007 | WO | WO 95/02369 A1 | 1/1995 |
| EP | 1839596 | A1 | 10/2007 | WO | WO 95/03743 A1 | 2/1995 |
| EP | 1402821 | B1 | 12/2007 | WO | WO 95/06817 A1 | 3/1995 |
| EP | 1872727 | A1 | 1/2008 | WO | WO 95/09576 A1 | 4/1995 |
| EP | 1897502 | A1 | 3/2008 | WO | WO 95/09577 A1 | 4/1995 |
| EP | 1330201 | B1 | 6/2008 | WO | WO 95/14436 A1 | 6/1995 |
| EP | 1702568 | B1 | 7/2008 | WO | WO 95/17855 A1 | 7/1995 |
| EP | 1943976 | A2 | 7/2008 | WO | WO 95/18383 A1 | 7/1995 |
| EP | 1593337 | B1 | 8/2008 | WO | WO 95/18572 A1 | 7/1995 |
| EP | 1970014 | A1 | 9/2008 | WO | WO 95/19739 A1 | 7/1995 |
| EP | 1980213 | A2 | 10/2008 | WO | WO 95/20360 A1 | 8/1995 |
| EP | 1759645 | B1 | 11/2008 | WO | WO 95/23557 A1 | 9/1995 |
| EP | 1693008 | B1 | 12/2008 | WO | WO 95/24865 A1 | 9/1995 |
| EP | 1759640 | B1 | 12/2008 | WO | WO 95/25471 A3 | 9/1995 |
| EP | 2000102 | A2 | 12/2008 | WO | WO 95/26562 A1 | 10/1995 |
| EP | 1749486 | B1 | 3/2009 | WO | WO 95/29639 A1 | 11/1995 |
| EP | 1721576 | B1 | 4/2009 | WO | WO 96/04858 A1 | 2/1996 |
| EP | 1745748 | B1 | 8/2009 | WO | WO 96/19151 A1 | 6/1996 |
| EP | 2090256 | A2 | 8/2009 | WO | WO 96/19152 A1 | 6/1996 |
| EP | 1607050 | B1 | 12/2009 | WO | WO 96/20652 A1 | 7/1996 |
| EP | 1566150 | B1 | 4/2010 | WO | WO 96/21119 A1 | 7/1996 |
| EP | 1813206 | B1 | 4/2010 | WO | WO 96/22055 A1 | 7/1996 |
| EP | 1769754 | B1 | 6/2010 | WO | WO 96/23448 A1 | 8/1996 |
| EP | 1535565 | B1 | 10/2010 | WO | WO 96/24301 A1 | 8/1996 |
| EP | 1702570 | B1 | 10/2010 | WO | WO 96/27337 A1 | 9/1996 |
| FR | 999646 | A | 2/1952 | WO | WO 96/35464 A1 | 11/1996 |
| FR | 1112936 | A | 3/1956 | WO | WO 96/39085 A1 | 12/1996 |
| FR | 2765794 | A | 1/1999 | WO | WO 96/39086 A1 | 12/1996 |
| GB | 939929 | A | 10/1963 | WO | WO 96/39087 A1 | 12/1996 |
| GB | 1210522 | A | 10/1970 | WO | WO 96/39088 A1 | 12/1996 |
| GB | 1217159 | A | 12/1970 | WO | WO 96/39089 A1 | 12/1996 |
| GB | 2109241 | A | 6/1983 | WO | WO 97/00646 A1 | 1/1997 |
| GB | 2272159 | A | 5/1994 | WO | WO 97/00647 A1 | 1/1997 |
| GB | 2284242 | A | 5/1995 | WO | WO 97/06582 A1 | 2/1997 |
| GB | 2336214 | A | 10/1999 | WO | WO 97/10763 A1 | 3/1997 |

| | | | | | | |
|---|---|---|---|---|---|---|
| WO | WO 97/10764 A1 | 3/1997 | | WO | WO 03/057058 A1 | 7/2003 |
| WO | WO 97/11648 A2 | 4/1997 | | WO | WO 03/063694 A1 | 8/2003 |
| WO | WO 97/11649 A1 | 4/1997 | | WO | WO 03/077769 A1 | 9/2003 |
| WO | WO 97/15237 A1 | 5/1997 | | WO | WO 03/079911 A1 | 10/2003 |
| WO | WO 97/24073 A1 | 7/1997 | | WO | WO 03/082126 A1 | 10/2003 |
| WO | WO 97/24993 A1 | 7/1997 | | WO | WO 03/088845 A2 | 10/2003 |
| WO | WO 97/30644 A1 | 8/1997 | | WO | WO 03/090630 A2 | 11/2003 |
| WO | WO 97/34533 A1 | 9/1997 | | WO | WO 03/094743 A1 | 11/2003 |
| WO | WO 97/37598 A1 | 10/1997 | | WO | WO 03/094745 A1 | 11/2003 |
| WO | WO 97/39688 A2 | 10/1997 | | WO | WO 03/094746 A1 | 11/2003 |
| WO | WO 98/17180 A1 | 4/1998 | | WO | WO 03/094747 A1 | 11/2003 |
| WO | WO 98/27880 A1 | 7/1998 | | WO | WO 03/101313 A1 | 12/2003 |
| WO | WO 98/30153 A1 | 7/1998 | | WO | WO 03/105698 A2 | 12/2003 |
| WO | WO 98/47436 A1 | 10/1998 | | WO | WO 03/105702 A2 | 12/2003 |
| WO | WO 99/03407 A1 | 1/1999 | | WO | WO 2004/006980 A2 | 1/2004 |
| WO | WO 99/03408 A1 | 1/1999 | | WO | WO 2004/019769 A1 | 3/2004 |
| WO | WO 99/03409 A1 | 1/1999 | | WO | WO 2004/021868 A2 | 3/2004 |
| WO | WO 99/12483 A1 | 3/1999 | | WO | WO 2004/028585 A2 | 4/2004 |
| WO | WO 99/12487 A1 | 3/1999 | | WO | WO 2004/032754 A2 | 4/2004 |
| WO | WO 99/12488 A1 | 3/1999 | | WO | WO 2004/032760 A2 | 4/2004 |
| WO | WO 99/15086 A1 | 4/1999 | | WO | WO 2004/032762 A1 | 4/2004 |
| WO | WO 99/15091 A1 | 4/1999 | | WO | WO 2004/032763 A2 | 4/2004 |
| WO | WO 99/23933 A2 | 5/1999 | | WO | WO 2004/034875 A2 | 4/2004 |
| WO | WO 99/23959 A1 | 5/1999 | | WO | WO 2004/047626 A1 | 6/2004 |
| WO | WO 99/25261 A1 | 5/1999 | | WO | WO 2004/047653 A2 | 6/2004 |
| WO | WO 99/29244 A1 | 6/1999 | | WO | WO 2004/049956 A2 | 6/2004 |
| WO | WO 99/34744 A1 | 7/1999 | | WO | WO 2004/052426 A2 | 6/2004 |
| WO | WO 99/45849 A1 | 9/1999 | | WO | WO 2004/056276 A1 | 7/2004 |
| WO | WO 99/48430 A1 | 9/1999 | | WO | WO 2004/056277 A1 | 7/2004 |
| WO | WO 99/51158 A1 | 10/1999 | | WO | WO 2004/062516 A1 | 7/2004 |
| WO | WO 00/24322 A1 | 5/2000 | | WO | WO 2004/078050 A2 | 9/2004 |
| WO | WO 00/24330 A1 | 5/2000 | | WO | WO 2004/078051 A2 | 9/2004 |
| WO | WO 00/41638 A1 | 7/2000 | | WO | WO 2004/086987 A1 | 10/2004 |
| WO | WO 00/48506 A1 | 8/2000 | | WO | WO 2004/096015 A2 | 11/2004 |
| WO | WO 00/53112 A2 | 9/2000 | | WO | WO 2004/096057 A2 | 11/2004 |
| WO | WO 00/54653 A1 | 9/2000 | | WO | WO 2004/103157 A2 | 12/2004 |
| WO | WO 00/57796 A1 | 10/2000 | | WO | WO 2004/105593 A1 | 12/2004 |
| WO | WO 00/64365 A1 | 11/2000 | | WO | WO 2004/105621 A1 | 12/2004 |
| WO | WO 00/72762 A1 | 12/2000 | | WO | WO 2004/112618 A2 | 12/2004 |
| WO | WO 00/72765 A1 | 12/2000 | | WO | WO 2004/112652 A2 | 12/2004 |
| WO | WO 01/03587 A1 | 1/2001 | | WO | WO 2005/027983 A2 | 3/2005 |
| WO | WO 01/05702 A1 | 1/2001 | | WO | WO 2005/037329 A2 | 4/2005 |
| WO | WO 01/10482 A1 | 2/2001 | | WO | WO 2005/044078 A2 | 5/2005 |
| WO | WO 01/35845 A1 | 5/2001 | | WO | WO 2005/055846 A1 | 6/2005 |
| WO | WO 01/54594 A1 | 8/2001 | | WO | WO 2005/072634 A2 | 8/2005 |
| WO | WO 01/58371 A1 | 8/2001 | | WO | WO 2005/078892 A1 | 8/2005 |
| WO | WO 01/62158 A2 | 8/2001 | | WO | WO 2005/096954 A2 | 10/2005 |
| WO | WO 01/62161 A1 | 8/2001 | | WO | WO 2005/112806 A2 | 12/2005 |
| WO | WO 01/62162 A1 | 8/2001 | | WO | WO 2005/112808 A1 | 12/2005 |
| WO | WO 01/62164 A2 | 8/2001 | | WO | WO 2005/115251 A2 | 12/2005 |
| WO | WO 01/62169 A2 | 8/2001 | | WO | WO 2005/117735 A1 | 12/2005 |
| WO | WO 01/78605 A2 | 10/2001 | | WO | WO 2005/122936 A1 | 12/2005 |
| WO | WO 01/91646 A1 | 12/2001 | | WO | WO 2006/044490 A2 | 4/2006 |
| WO | WO 02/07608 A2 | 1/2002 | | WO | WO 2006/044581 A2 | 4/2006 |
| WO | WO 02/07618 A1 | 1/2002 | | WO | WO 2006/044810 A2 | 4/2006 |
| WO | WO 02/17799 A1 | 3/2002 | | WO | WO 2006/051252 A1 | 5/2006 |
| WO | WO 02/19920 A1 | 3/2002 | | WO | WO 2006/059067 A1 | 6/2006 |
| WO | WO 02/19932 A1 | 3/2002 | | WO | WO 2006/083748 A1 | 8/2006 |
| WO | WO 02/30297 A2 | 4/2002 | | WO | WO 2006/092563 A1 | 9/2006 |
| WO | WO 02/32322 A2 | 4/2002 | | WO | WO 2006/092565 A1 | 9/2006 |
| WO | WO 02/36028 A1 | 5/2002 | | WO | WO 2006/115958 A1 | 11/2006 |
| WO | WO 02/43571 A2 | 6/2002 | | WO | WO 2006/125940 A1 | 11/2006 |
| WO | WO 02/058568 A1 | 8/2002 | | WO | WO 2006/132992 A1 | 12/2006 |
| WO | WO 02/060328 A1 | 8/2002 | | WO | WO 2007/002180 A2 | 1/2007 |
| WO | WO 02/067785 A2 | 9/2002 | | WO | WO 2007/016290 A2 | 2/2007 |
| WO | WO 02/098302 A1 | 12/2002 | | WO | WO 2007/018898 A2 | 2/2007 |
| WO | WO 03/000138 A2 | 1/2003 | | WO | WO 2007/098220 A2 | 8/2007 |
| WO | WO 03/001329 A2 | 1/2003 | | WO | WO 2007/121579 A1 | 11/2007 |
| WO | WO 03/013363 A1 | 2/2003 | | WO | WO 2007/137304 A2 | 11/2007 |
| WO | WO 03/015604 A2 | 2/2003 | | WO | WO 2007/139734 A2 | 12/2007 |
| WO | WO 03/020106 A2 | 3/2003 | | WO | WO 2007/142625 A2 | 12/2007 |
| WO | WO 03/020139 A2 | 3/2003 | | WO | WO 2008/021969 A2 | 2/2008 |
| WO | WO 03/024339 A1 | 3/2003 | | WO | WO 2008/039270 A1 | 4/2008 |
| WO | WO 03/079909 A3 | 3/2003 | | WO | WO 2008/045383 A2 | 4/2008 |
| WO | WO 03/030743 A2 | 4/2003 | | WO | WO 2008/109125 A1 | 9/2008 |
| WO | WO 03/037193 A1 | 5/2003 | | | | |
| WO | WO 03/047436 A3 | 6/2003 | | | | |
| WO | WO 03/055402 A1 | 7/2003 | | | | |
| WO | WO 03/057048 A1 | 7/2003 | | | | |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

International Search Report for PCT/US2010/059034, Jun. 1, 2011 (8 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

* cited by examiner

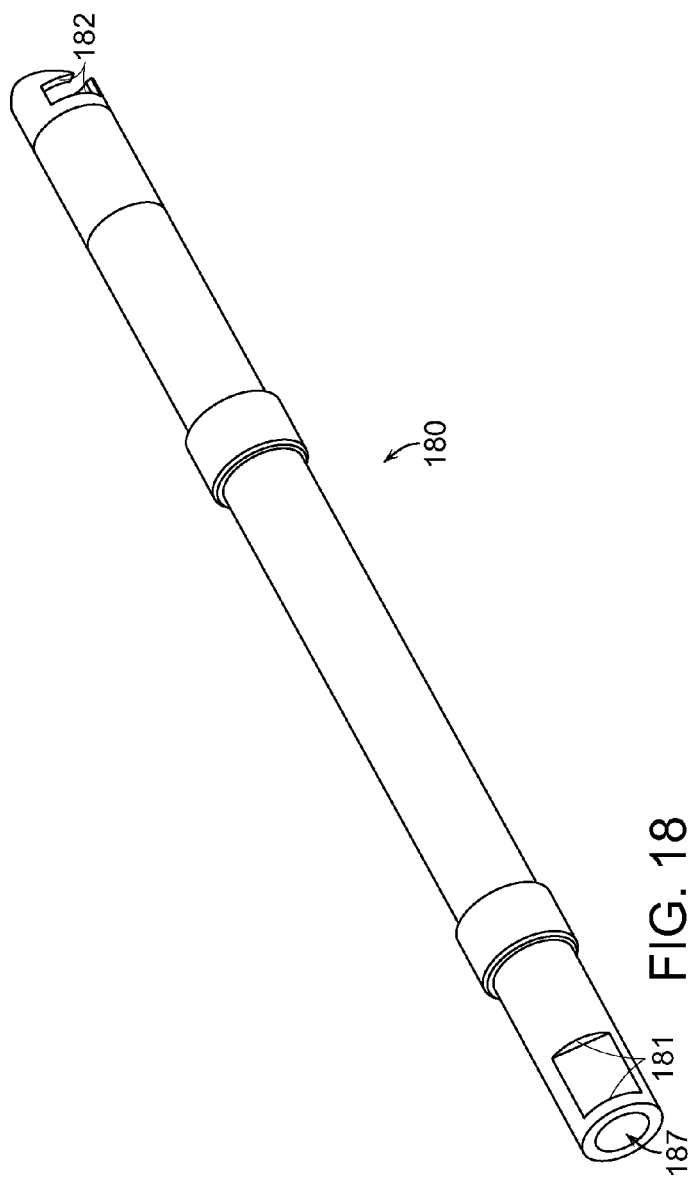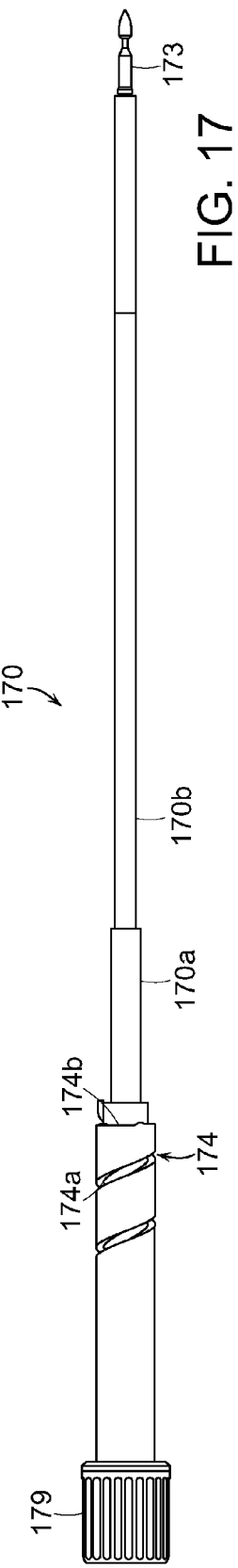

SURGICAL STAPLER WITH DISCRETE STAPLE HEIGHT ADJUSTMENT AND TACTILE FEEDBACK

BACKGROUND

The embodiments relate, in general, to surgical staplers, and, more particularly, to a circular stapler including a discrete staple height adjustment.

In certain types of surgical procedures, the use of surgical staples has become the preferred method of joining tissue and, as such, specially configured surgical staplers have been developed for these applications. For example, intra-luminal or circular staplers have been developed for use in a surgical procedure known as an anastomosis. Circular staplers useful for performing an anastomosis are disclosed, for example, in U.S. Pat. Nos. 5,104,025; 5,205,459; 5,285,945; and 5,309,927, and in U.S. patent application Ser. No. 12/408,905, which are each herein incorporated by reference in their respective entireties.

One form of an anastomosis comprises a surgical procedure wherein sections of intestine are joined together after a diseased portion has been excised. The procedure requires re-joining the ends of the two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform an anastomosis.

In general, a conventional circular stapler typically consists of an elongated shaft that has a proximal actuating mechanism and a distal stapling mechanism mounted to the shaft. The distal stapling mechanism commonly consists of a fixed stapling cartridge that contains a plurality of staples configured in a concentric circular array. A round cutting knife is concentrically mounted in the cartridge interior to the staples for axial travel therein. Extending axially from the center of the cartridge is a movable trocar shaft that is adapted to have a staple anvil removably coupled thereto. The anvil is configured to form the ends of the staples as they are driven into it. The distance between a distal face of the staple cartridge and the staple anvil is controlled by an adjustment mechanism mounted to the proximal end of the stapler shaft for controlling the axial movement of the trocar. Tissue clamped between the staple cartridge and the staple anvil is simultaneously stapled and cut when the actuating mechanism is activated by the surgeon.

Generally, in the performance of a surgical anastomotic stapling operation, two pieces of lumen or tubular tissue, e.g., intestinal tissue, are attached together by a ring of staples. The two pieces of tubular tissue may be attached end to end or one piece of tubular tissue may be attached laterally around an opening formed in the side of another piece of tubular tissue. In performing the anastomosis with a stapling instrument, the two pieces of tubular tissue are clamped together between the anvil and the staple cartridge. A staple pusher is advanced to drive the staples into the tissue and form the staples against the anvil. Also, the circular knife is advanced to cut the excess tissue clamped between the anvil and the staple holder. As a result, a donut-shaped section of tissue is severed from each lumen and remains on the anvil shaft. The tubular tissue joined by the circular ring of staples is unclamped by advancing the anvil shaft distally to move the anvil away from the staple holder. The stapling insrument is removed by pulling the anvil through the circular opening between the pieces of tubular tissue attached by the ring of staples.

Further, when performing a lower colon procedure using a circular stapler, the intestine is typically stapled using a conventional surgical stapler with double rows of staples being emplaced on either side of the diseased portion of intestine to be removed. The target section is simultaneously cut as the adjoining end is stapled. After removing the diseased portion, the surgeon typically inserts the anvil into the proximal end of the lumen, proximal of the staple line. This is done by inserting the anvil head into an entry port cut into the proximal lumen by the surgeon. On occasion, the anvil can be placed transanally, by placing the anvil head on the distal end of the stapler and inserting the instrument through the rectum. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby clamping the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, the concentric circular knife blade is driven through the intestinal tissue ends, cutting the ends adjacent to the inner row of staples. The surgeon then withdraws the stapler from the intestine and the procedure is complete.

During the above-described surgical procedures, it is desirable to properly form staples within a range of staple heights such that they are retained in the tissue and prevent leakage and bleeding and to achieve "tissue-to-tissue" contact which promotes tissue healing. In general, by controlling the distance or gap between the anvil and the cartridge, better stapling and healing results may be achieved. While some surgical staplers are equipped with a visual readout indicating staple height, a surgeon may need to focus on many different items during surgery. Further, once the anvil has been properly positioned, it is necessary that the anvil not move during firing, otherwise proper staple formation could be adversely affected.

The foregoing discussion is intended only to illustrate the present field and should not be taken as a disavowal of claim scope.

SUMMARY

In various embodiments, a surgical stapler is provided. In at least one embodiment, the surgical stapler can comprise a body, a stapling head assembly, a drive system, an anvil, and an anvil adjustment assembly. In these embodiments, the body can comprise a handle portion and a shaft portion extending from the handle portion. Further, in these embodiments, the stapling head assembly can be releasably coupled to the shaft portion and the stapling head assembly can also comprise a staple cartridge for supporting one or more surgical staples, and at least one staple driver for engaging and driving the staples from the staple cartridge. Moreover, in these embodiments, the drive system may be configured to apply drive motions to the staple driver. Additionally, in these embodiments, the anvil may be movably supported relative to the staple cartridge for axial movement toward and away from the staple cartridge. Also, in these embodiments, the anvil adjustment assembly may be configured to selectively adjust an axial position of the anvil relative to the staple cartridge. Further, in these embodiments, the anvil adjustment assembly can comprise an adjustment shaft and a trocar coupled to the adjustment shaft for travel therewith, and the trocar can be configured for removable attachment to the anvil. Moreover, in these embodiments, one of the adjustment shaft or the body can comprise an engagement portion, and the other of the adjustment shaft or the body can comprise a screw surface including at least one ramp portion, at least one dwell portion, and at least one delimiter separating the at least one dwell portion from the at least one ramp portion. Additionally, in these embodiments, the at least one ramp portion can be configured to operably engage the engagement portion to cause the adjustment shaft to move relative to the body when the adjustment shaft is rotated.

In at least one embodiment, a surgical stapler is provided that can comprise a body, a stapling head operably coupled to the body, an anvil movably supported relative to the stapling head for selective travel toward and away from the stapling head, and an anvil adjustment shaft supported by the body for selectively adjusting a position of the anvil relative to the stapling head. Further, in these embodiments, one of the adjustment shaft or the body can comprise an engagement portion, and the other of the adjustment shaft or the body can comprise a screw surface including a first portion and a second portion. Moreover, in these embodiments, the first portion can be configured to operably engage the engagement portion to cause the adjustment shaft to move relative to the body when the adjustment shaft is rotated. Additionally, in these embodiments, at least one delimiter can separate the first portion from the second portion.

In at least one embodiment, a surgical stapler is provided that can comprise a body, a stapling head operably coupled to the body, an anvil movably supported relative to the stapling head for selective travel toward and away from the stapling head, and an anvil adjustment shaft supported by the body for selectively adjusting a position of the anvil relative to the stapling head. Further, in these embodiments, one of the adjustment shaft or the body can comprise an engagement portion, and the other of the adjustment shaft or the body can comprise a screw surface including at least one ramp portion and at least one dwell portion. Moreover, in these embodiments, the at least one ramp portion can be configured to operably engage the engagement portion to cause the adjustment shaft to move relative to the body when the adjustment shaft is rotated.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 17 is a side view of an anvil adjustment shaft of the surgical stapler of FIG. 16.

FIG. 18 is a perspective view of a drive bar of the surgical stapler of FIG. 16.

DETAILED DESCRIPTION

Figure 1:
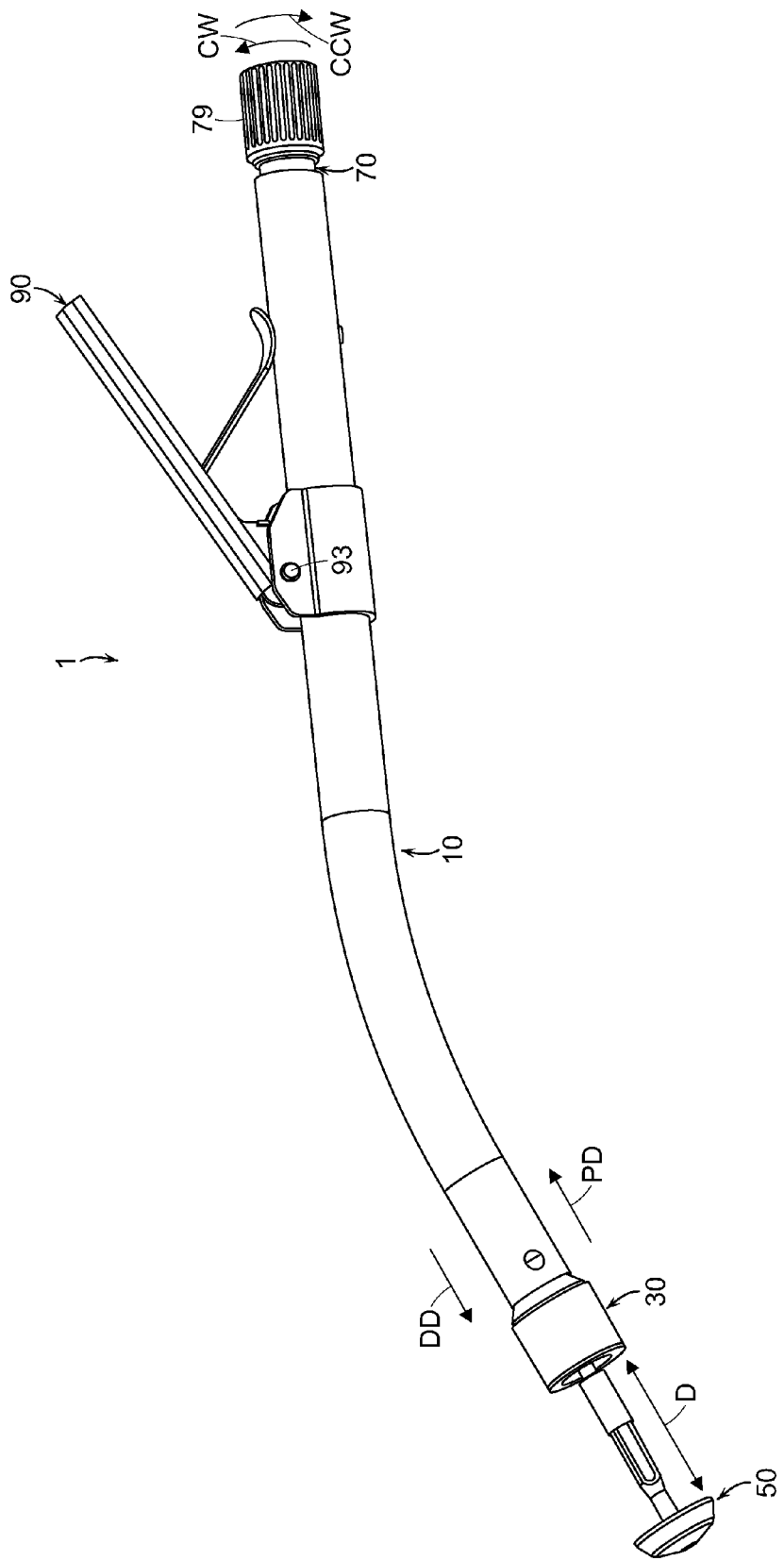
FIG. 1 is a perspective view of a non-limiting embodiment of a surgical stapler including a circular stapling head and an anvil in a first position.
Figure 2:
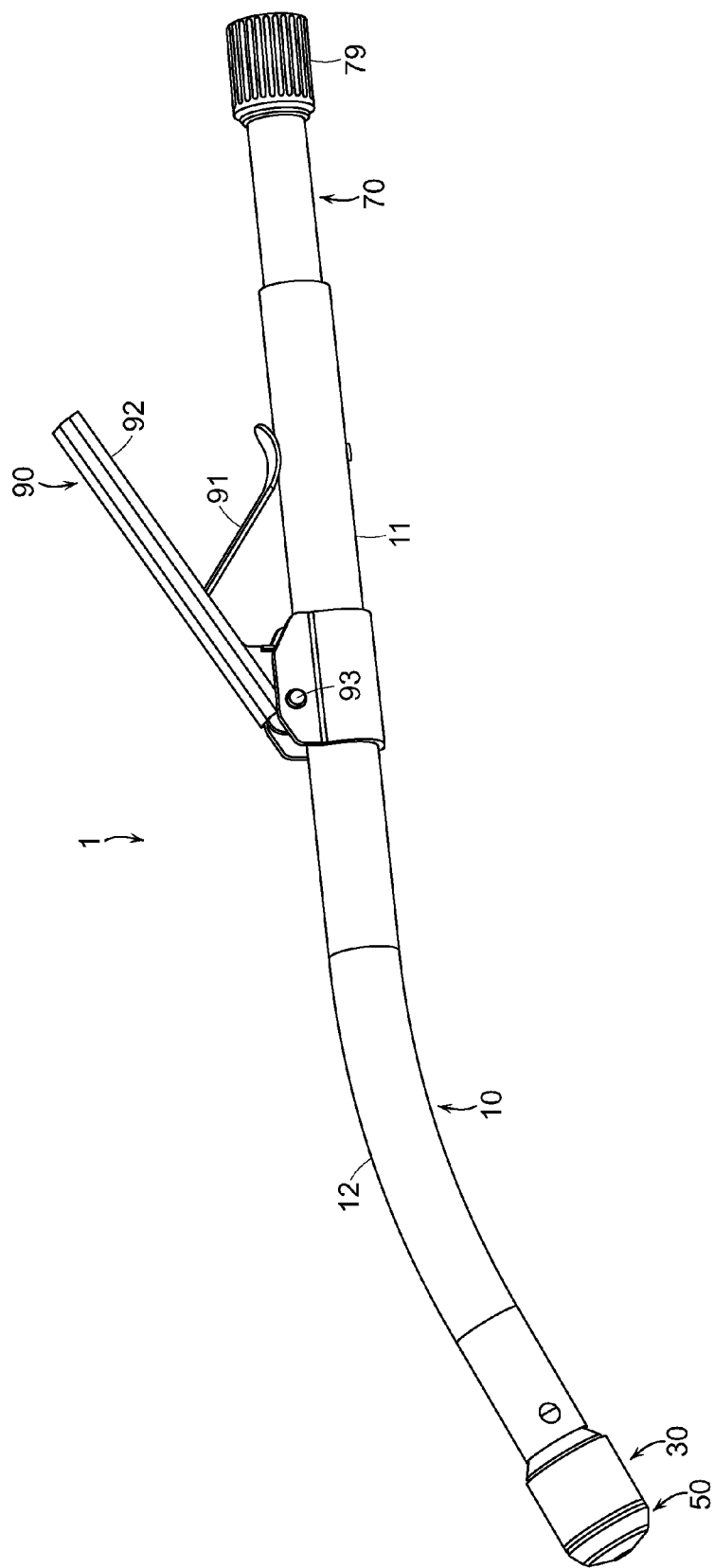
FIG. 2 is a perspective view of the surgical stapler of FIG. 1 with the anvil shown in a second position.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Further, where an ordering of steps in a process is indicated, such ordering may be rearranged or the steps may be carried out contemporaneously as desired unless illogical or the listed order is explicitly required. Such modifications and variations are intended to be included within the scope of the appended claims.

In the following description, like reference characters designate like or corresponding parts throughout the several views. Also in the following description, it is to be understood that terms such as "forward," "rearward," "front," "back," "right," "left," "over," "under," "upwardly," "downwardly," "proximally," "distally," and the like are words of convenience and are not to be construed as limiting terms. The description below is for the purpose of describing various embodiments and is not intended to limit the appended claims.

The various embodiments generally relate to various surgical staplers configured to seal tissue and, in at least one embodiment, cut tissue also. Such surgical staplers may be configured to function through a natural orifice, such as the anus, mouth and/or vagina, or through an incision cut through a body wall. Further, such surgical staplers may be designed as endoscopic tools, including laparoscopic tools.

Focusing now on one non-limiting embodiment, as can be seen in FIGS. 1-4, a circular stapler 1 is provided that includes a tubular or circular body 10, a stapling head 30 operably coupled to the body 10, an anvil 50, an anvil adjustment shaft 70 supported by the body 10, and a trigger 90 movably coupled to the body 10. The anvil 50 may be movably supported relative to the stapling head assembly for selective travel toward and away from the stapling head 30. Further, the anvil adjustment shaft 70 may be supported by the body 10 to selectively adjust a position of the anvil relative to the stapling head. Therefore, as will be explained in more detail below, the adjustment shaft 70 may be operably coupled to the anvil 50 to effect movement of the same. For example, the adjustment shaft 70 may be rotated, via a knob 79 of the adjustment shaft, about its longitudinal axis, in a first rotation direction, such as a clockwise "CW" direction, to cause the shaft 70 and the anvil 50 to move or translate in a distal direction "DD," relative to the body 10, from a first position shown in FIG. 1 to a second position shown in FIG. 2. Likewise, the adjustment shaft 70 may be rotated in a second rotational direction, such as a counterclockwise "CCW" direction, to cause the shaft 70 and the anvil 50 to move or translate in a proximal direction "PD," relative to the body 10, from the second position shown in FIG. 2 to the first position shown in FIG. 1. It is to be understood that the anvil 50 may be positioned anywhere between or outside the positions shown in FIGS. 1-2, as allowed by the surgical stapler 1. Further, in at least one embodiment, as explained in more detail below, the adjustment shaft 70 may be configured to move the anvil 50 to at least one predetermined distance from the stapling head and/or to provide tactile feedback to a user.

Figure 7C:
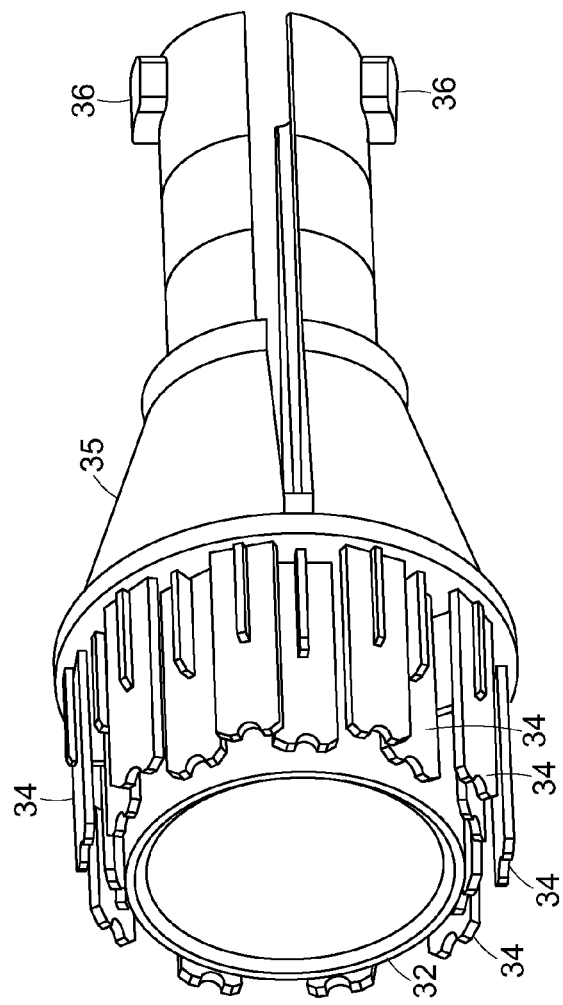
FIG. 7C is a front perspective view of a cutting member and staple drivers of the stapling head assembly of FIG. 7A.
Figure 7B:
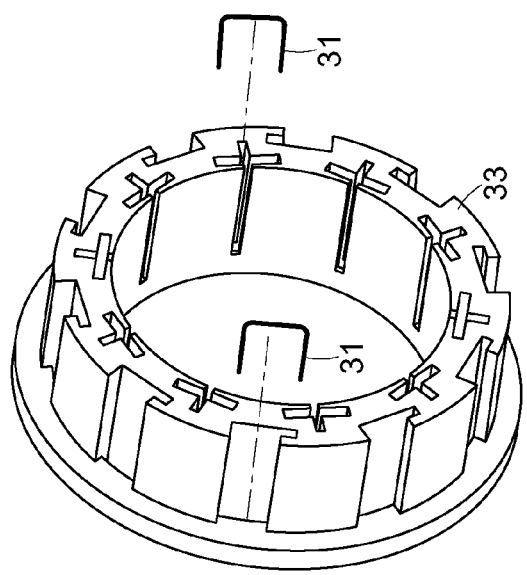
FIG. 7B is a rear perspective view of a staple cartridge of the stapling head assembly of 7A; two staples are shown removed from staple cavities of the cartridge.

When the trigger 90 is activated, a drive system may be actuated within the body 10 so that staples 31 (see FIGS. 3 and 7B) may be expelled from the stapling head 30 into forming contact with the anvil 50. Simultaneously, a cutting member 32 (see FIG. 7C), that is operably supported within the head 30, acts to cut tissue held within the circumference of the stapled tissue. The stapler 10 is then pulled through the tissue leaving stapled tissue in its place. Further, the trigger 90 may include a spring 91 extending from a lever 92 such that when lever 92 is squeezed or otherwise moved towards body 10 about hinge pin 93, the lever 91 is biased back away from the body 10 and the knife 70 is automatically retracted upon release of the lever 92.

Figure 3:
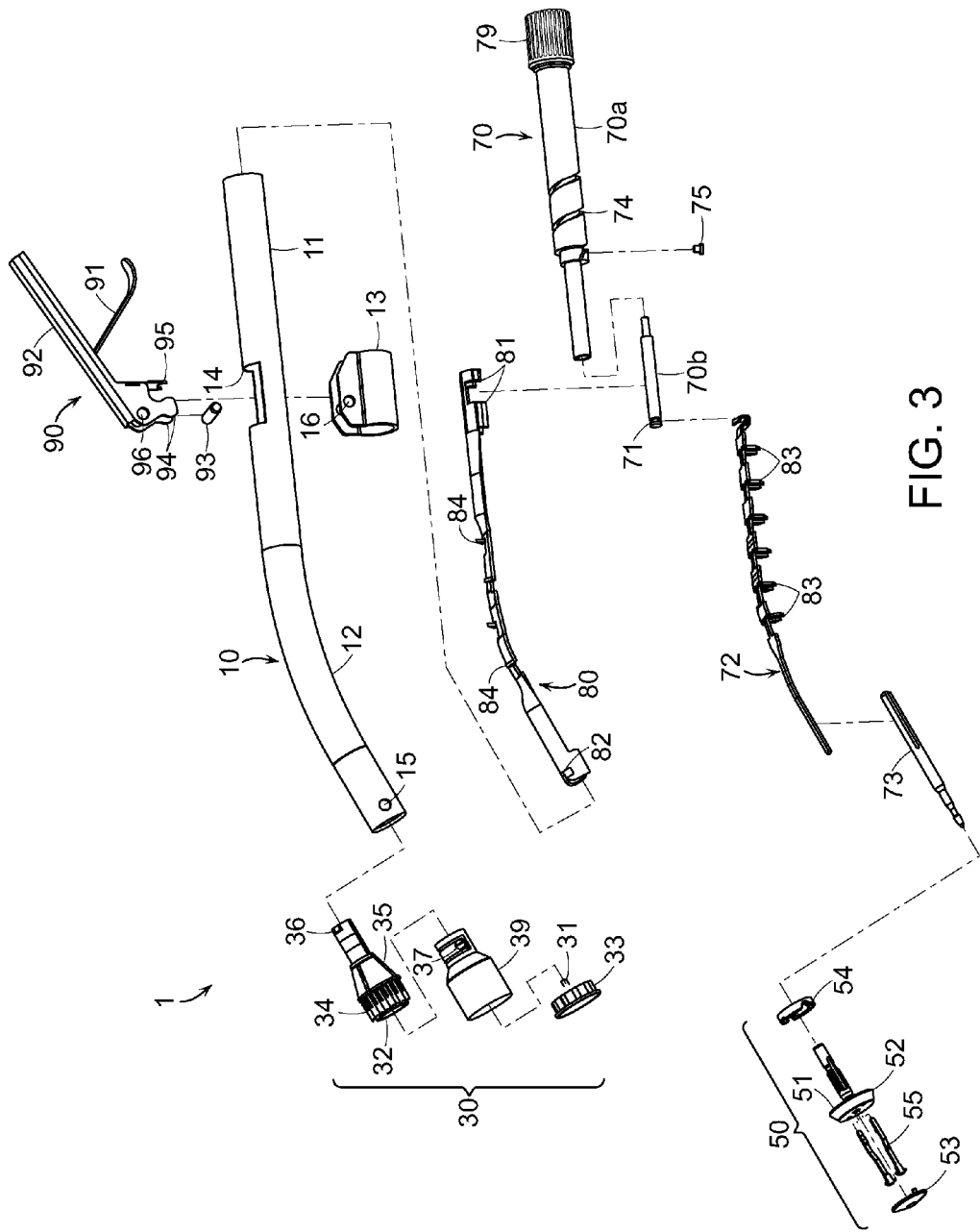
FIG. 3 is an exploded view of the surgical stapler of FIG. 1.

Referring to FIG. 3, the body 10 may include a handle portion 11 and a curved shaft portion 12. While the present embodiment illustrates a curved shaft portion 12, the shaft portion may also be straight or linear (see, e.g., FIG. 16, discussed below). The handle portion 11 may be adapted to receive trigger 90 via a saddle attachment 13 that may further include holes 16 (see FIG. 3) with which to receive hinge pin 93 which may also be received in holes 96 of the trigger 90. The handle portion 11 may further define an opening 14 at the top of the body 10 through which a portion of the trigger 90 may be positioned. For example, cam surfaces 94 and a lockout stem 95 may extend through the opening 14. As will be explained in more detail below, cam surfaces 94 may be configured to actuate the drive system when the trigger 90 is moved relative to the handle portion 11, and the lockout stem 95 may prevent inadvertent firing of the cutting member 32 and/or staples 31 before the anvil 50 is in an appropriate position such that staples may be formed between the anvil 50 and the stapling head 30.

Figure 4:
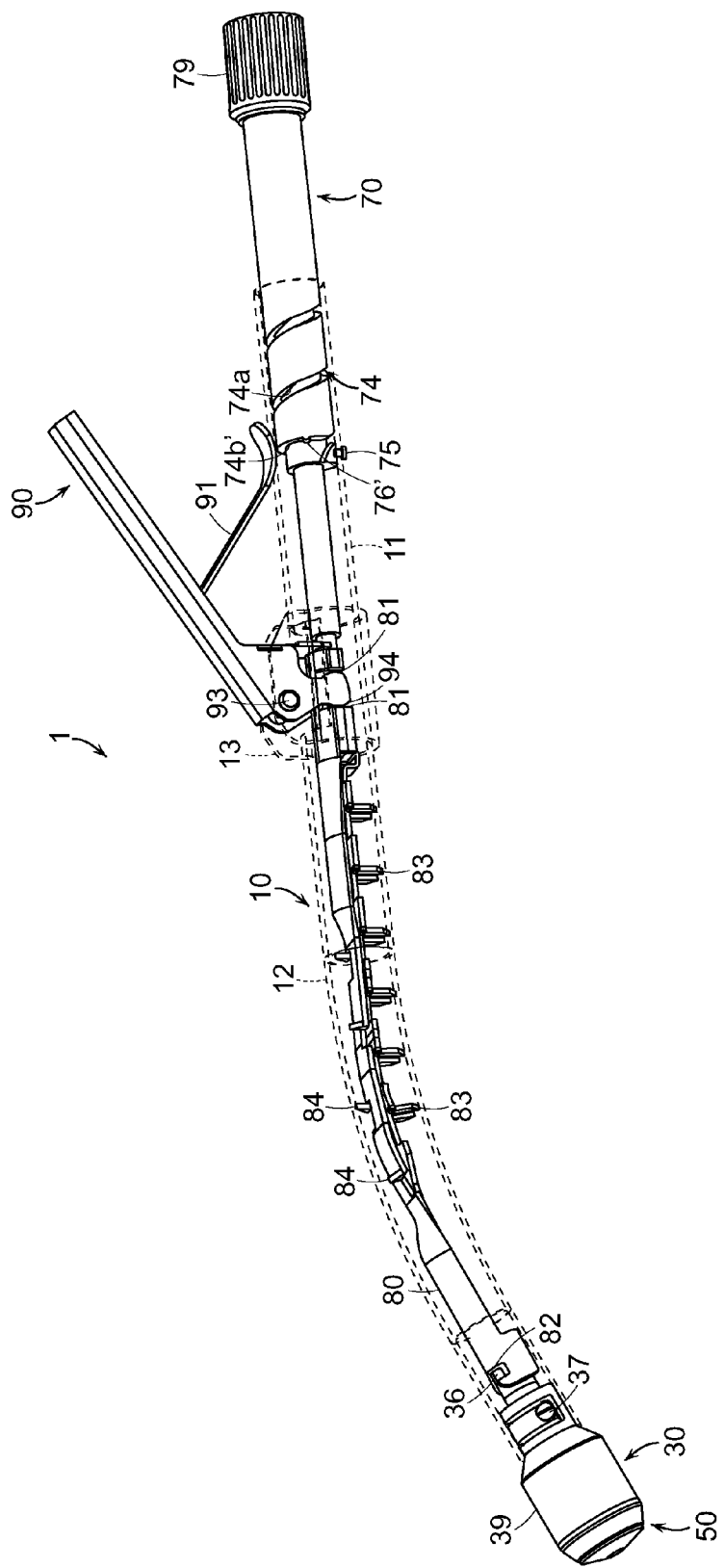
FIG. 4 is a perspective view of the surgical stapler of FIG. 1 with a body of the stapler shown in dotted lines to better illustrate the stapler's components within the body.

Referring to FIGS. 3 and 4, the drive system may comprise drive band 80 extending axially between the trigger's cam surfaces 94 and tabs 36 of the stapling head 30, within the body's shaft portion 12. Drive band 80 may include proximal drive surfaces 81 and distal drive surfaces 82. Thus actuation of the trigger may cause the cam surfaces 94 to rotate and push proximal drive surfaces 81 such that the drive band 80 moves in an axial direction towards or away from anvil 50. The stapling head's tabs 36 may be coupled within the drive band's distal drive surfaces 82, which may take the form of notches to releasably receive tabs 36.

Referring to FIGS. 4 and 7A-7C, the stapling head 30 may include an assembly comprising a staple cartridge 33 for supporting one or more staples 31, at least one staple driver 34 for engaging and driving the staples 31 from the cartridge 33, and a cutting member 32, e.g., a knife, movably supported in the stapling head 30. In at least one embodiment, the staple drivers 34 and the cutting member 32 may be integrally connected and/or formed. For example, the staple drivers 34 and cutting member 32 may extend from a core 35, each of which may be formed from the same material. In any event, actuation of the drive band 80 towards staple cartridge 33 and/or anvil 50 may cause the stapling head's tabs 36, which may extend from core 35, and, thus, the cutting member 32 and the staple drivers 34 to move towards anvil 50. Further, the stapling head 30 may also comprise a casing 39 that is configured to hold the staple cartridge 33 and movably receive the staple drivers 34, cutting member 32, and/or core 35 therethrough. The casing 39 may additionally include release buttons 37 that are configured to flexibly deflect and allow the stapling head 30 to be releasably attached to the body's shaft portion 12 at corresponding holes 15 (see FIG. 3) formed therein. Accordingly, referring to FIG. 4, the stapling head 30 may be removed by pressing on buttons 37, then turning the head 30 such that tabs 36 are released from the notches formed by the distal driving surfaces 82 of the drive band 80, and finally pulling the stapling head 30 away from the body 10.

Focusing now on the adjustment of the anvil 50 and referring to FIG. 3, in various embodiments and as noted above, the anvil 50 may be movably supported relative to the staple cartridge 33 such that the anvil may be moved axially toward and away from the staple cartridge 33. In more detail, the surgical stapler 1 may comprise an anvil adjustment assembly for selectively adjusting an axial position of the anvil 50 relative to the staple cartridge 33. The anvil adjustment assembly may comprise adjustment shaft 70 and a trocar 73 coupled to the adjustment shaft 70 for travel therewith. The adjustment shaft 70 may comprise a proximal portion 70a and a distal portion 70b, which may be connected together to form shaft 70. Alternatively, proximal and distal portions 70a, 70b may be unitary and integrally formed from the same piece of material (see, e.g., adjustment shaft 170 depicted in FIG. 17 and discussed below). Additionally, the adjustment shaft 70 may further comprise an annular groove 71 located at distal portion 70b which may be clipped or otherwise freely connected to a proximal end of an anvil adjustment band 72. By freely connected, it is to be understood that the adjustment band 72 may not rotate while the adjustment shaft 70 rotates; however, the adjustment band 72 may still translate along with the shaft 70. A distal end of the adjustment band 72 may be also attached to trocar 73. Accordingly, axial movement or translation of adjustment shaft 70 with respect to body 10 may cause the trocar 73 to also axially move or translate with respect to body 10.

Referring to FIGS. 3 and 4, one or both of anvil adjustment band 72 and drive band 80 may include tabs 83 and 84, respectively, that are bent or otherwise projecting toward body 10. Tabs 83, 84 may assist in allowing bands 72, 80 to travel through the body's curved shaft portion 12 while filling space and maintaining an appropriate axial position therein.

Figure 6:
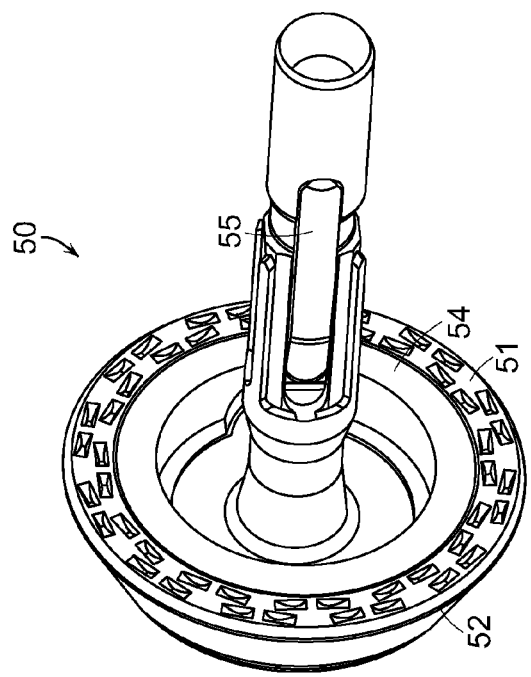
FIG. 6 is a rear perspective view of the anvil of the surgical stapler of FIG. 1.

Further, referring to FIGS. 3 and 6, as is known in the field, the trocar 73 may be removably attached to the anvil 50 by leaf or spring clips 55 coupled to the anvil and/or trocar. In other words, the anvil may be removed from the trocar by pressing, pulling, or otherwise manipulating the spring clips 55. Contrarily, the trocar may be snapped into the anvil by moving the trocar into the anvil such that the spring clips 55 releasably hold the anvil on the trocar. Thus, axial movement of the anvil adjustment shaft 70 with respect to body 10 may also axially move or translate anvil 50 with respect to body 10. Further, the anvil may also include a shroud 53 coupled to an anvil body 52 (see FIG. 3) and a washer 54 that is sheared during firing of the cutting member 32, as discussed above. The washer 54 may be made of plastic and may serve as a cutting surface against which tissue may be severed.

Figure 5:
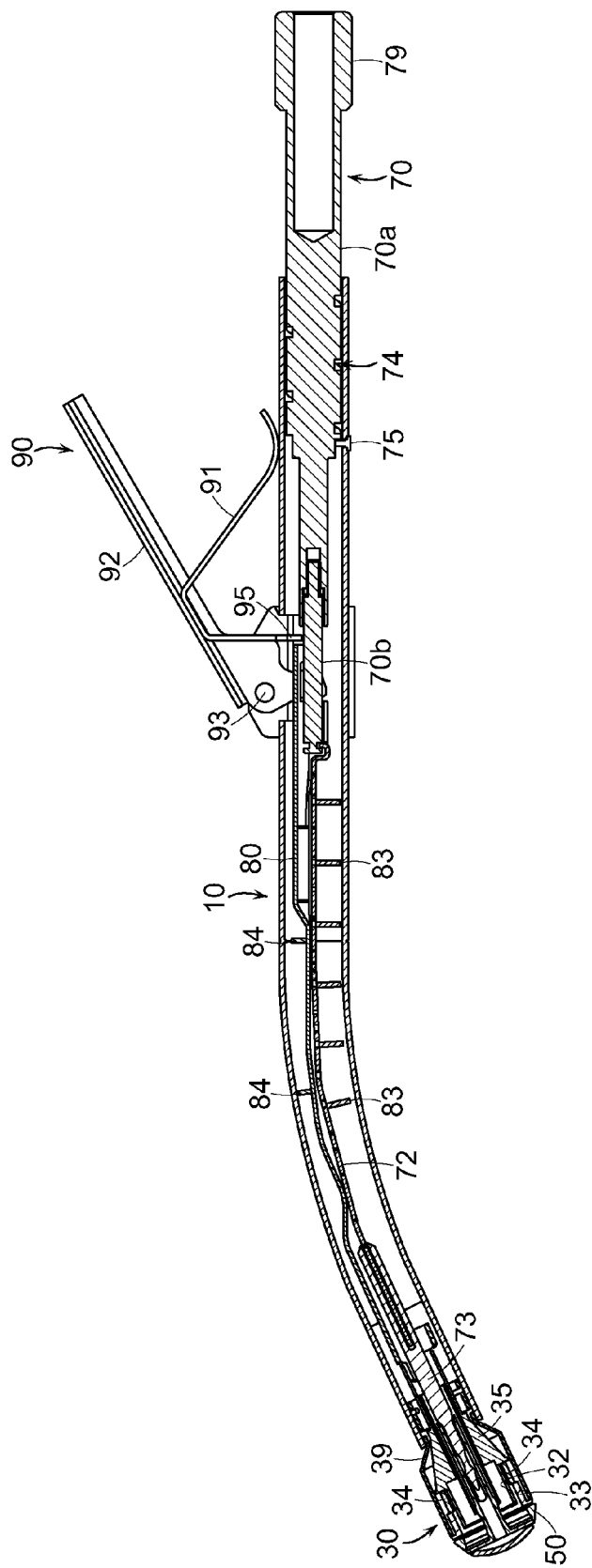
FIG. 5 is a cross-sectional view of the surgical stapler of FIG. 1.
Figure 7A:
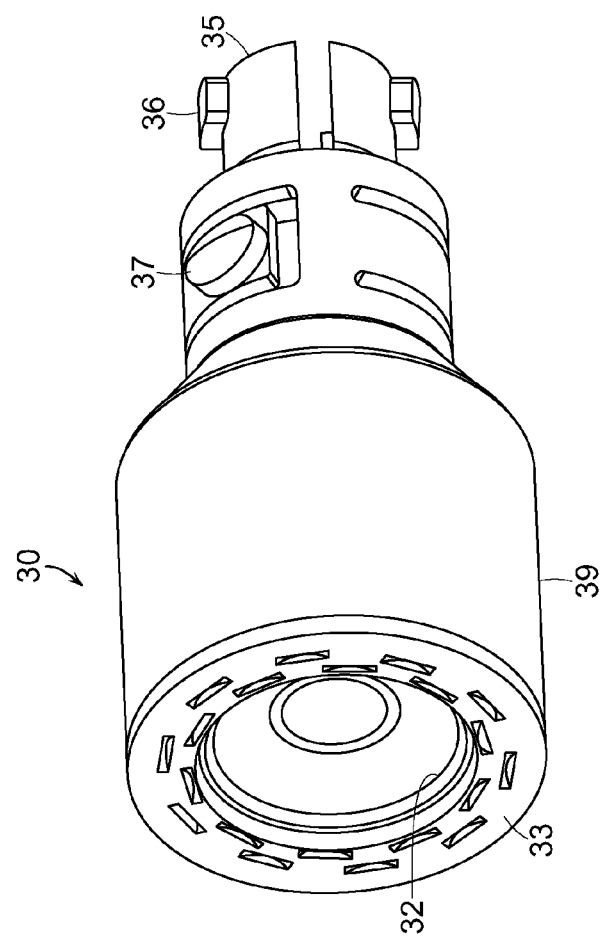
FIG. 7A is a front perspective view of a stapling head assembly of the surgical stapler of FIG. 1.

Referring now to FIGS. 3-5, the anvil adjustment shaft 70 may be configured to be rotated, as explained above, such that the shaft 70 translates relative to the body 10. In more detail and in at least one embodiment, the anvil adjustment shaft 70 may comprise a screw surface 74 that operably engages an engagement portion of the body 10, such as a screw pin 75 fixed to the body 10 via a hole in the same. The screw surface 74 may be defined by a channel formed in adjustment shaft 70 that is sized and configured to receive at least a portion of pin 75 therein. The anvil adjustment shaft 70 may be rotated about its longitudinal axis L (see FIG. 8) such that the screw surface 74 contacts and is moved over the pin 75, thereby causing the anvil adjustment shaft 70 to translate with respect to the body 10. While pin 75 is described in the present embodiment, any other suitable thread mating portion or component, such as a protrusion, thread, and the like, may be used to engage the screw surface in place of or in addition to pin 75. In any event, rotating the adjustment shaft 70 about its longitudinal axis may cause the shaft 70 and, hence, trocar 73 and anvil 50 to also translate or move axially with respect body 10 and/or stapling head 30.

As mentioned above, in various embodiments, the adjustment shaft 70 may be configured to move the anvil 50 to at least one predetermined distance from the stapling head 30. In more detail, and focusing now on FIG. 8, which shows only the adjustment shaft 70, the adjustment shaft's screw surface 74 may include at least one ramp portion and at least one dwell portion. For example, the screw surface 74 may comprise a first, ramp portion 74a and a second, dwell portion or portions 74b. At least one delimiter, such as delimiter 76, may also separate the ramp portion 74a from the dwell portion 74b. As will be discussed in more detail below, the ramp portion 74a may allow the adjustment shaft to translate with respect to the body 10 (see FIG. 4), dwell portion 74b may provide a predetermined distance to maintain the position of the anvil 50 from the stapling head 30 (see FIG. 2), and the delimiter 76 may provide tactile feedback to a user rotating the anvil adjustment shaft 70 as well as a transition between the ramp and dwell portions. Further, in at least one embodiment, the ramp portion 74a may be at least partially helical in shape.

Figure 8:
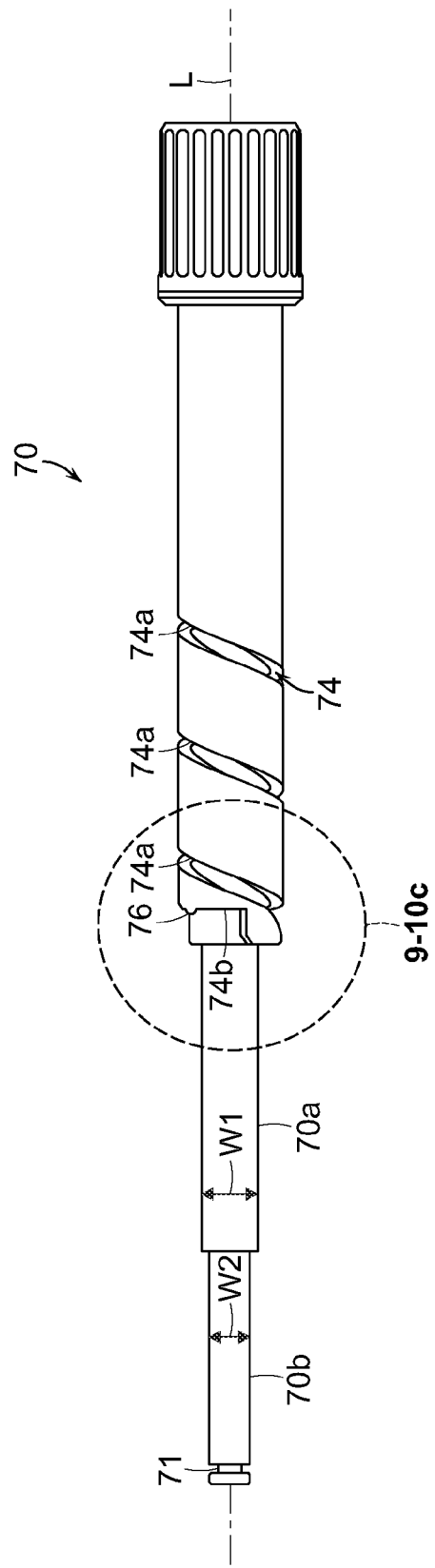
FIG. 8 is a side view of an anvil adjustment shaft of the surgical stapler of FIG. 1.

Continuing, the circle drawn in dashed lines in FIG. 8 represents the approximate portion of the anvil adjustment shaft 70 that is shown in FIGS. 9 and 10A-10C. Focusing now on FIG. 9, the ramp portion 74a of screw surface 74 may lead into at least one dwell portion. As illustrated and in at least one embodiment, the screw surface 74 may further comprise three dwell portions, first dwell portion 74b', second dwell portion 74b'', and third dwell portion 74b'''. Rotation of the anvil adjustment shaft 70 about its longitudinal axis may cause the screw surface 74 to pass along pin 75 (see FIG. 5) such that the shaft 70 translates with respect to the body 10 (again, see FIG. 5). Further, as the shaft 70 is rotated clockwise CW, for example, the screw surface 74 may move along pin 75 such that the pin 75 contacts the ramp portion and then the first dwell portion 74b'. Then, as the shaft 70 is again rotated clockwise CW, the pin may contact the second dwell portion 74b''. Thereafter, additional rotation of the shaft 70 clockwise CW may cause the pin to contact the third dwell portion 74b'''. As will be explained in more detail below, each dwell portion may be at a different angular configuration compared to the ramp portion 74a.

Further, each dwell portion 74b', 74b'', and 74b''' may be at a different longitudinal position along anvil adjustment shaft 70 to provide predetermined, discrete staple forming heights. For example, referring to FIG. 10A, the first dwell portion 74b' may be at a first distance $L_1$ from a transverse ledge 77 of the shaft assembly. The second dwell portion 74b'' may be at a second distance $L_2$ from the transverse ledge 77, and the third dwell portion 74b''' may be at a third distance $L_3$ from the transverse ledge 77. Any reference point or plane, including transverse ledge 77 may be used to establish the aforementioned distances. In any event, the first distance $L_1$ may be greater than the second distance $L_2$, which may be greater than the third distance $L_3$, or $L_1 > L_2 > L_3$. Alternatively, although now shown, the distances may be in other comparative orders, such as $L_1 > L_3 > L_2$, $L_2 > L_1 > L_3$, $L_2 > L_3 > L_1$, $L_3 > L_2 > L_1$, or $L_3 > L_1 > L_2$. Further, each of the dwell distances $L_1$, $L_2$, and $L_3$ may be uniform over their respective dwell portions 74b', 74b'', and 74b'''. In other words, referring to FIG. 10B, for example, while the screw surface's ramp portion 74a may slope at a ramp or helix angle $\alpha$ of less than 90 degrees relative to the adjustment shaft's longitudinal axis L, each dwell portion (e.g., 74b'' in FIG. 10B) may be substantially perpendicular to the longitudinal axis L, or define an angle $\theta$ that is approximately 90 degrees with respect to the axis L. Further, referring to FIGS. 9 and 10A-10C, the dwell portions 74b', 74b'', 74b''' may otherwise be steps defining predetermined, discrete staple heights, as discussed below. When measuring the aforementioned angles with respect to longitudinal axis L, it should be understood that such measurements may be made with respect to a plane that is tangential to a portion of screw surface 74 and that plane's intersection with longitudinal axis L, which, for the purposes of clarity, is shown over the length of the anvil adjustment shaft shown in FIGS. 10A-10C. For example, referring to FIG. 10B again, helix angle $\alpha$ is defined between tangential plane "TP," that is perpendicular to the plane of the page of FIG. 10B, and longitudinal axis L.

Figure 10C:
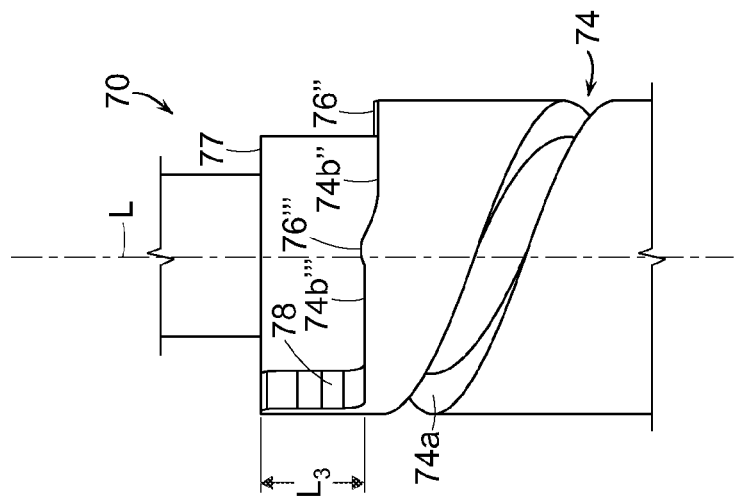
FIGS. 10A-10C are a series of side views of a portion of the anvil adjustment shaft of FIG. 8, each showing a progression of a screw surface as the shaft is rotated about its longitudinal axis.
Figure 10B:
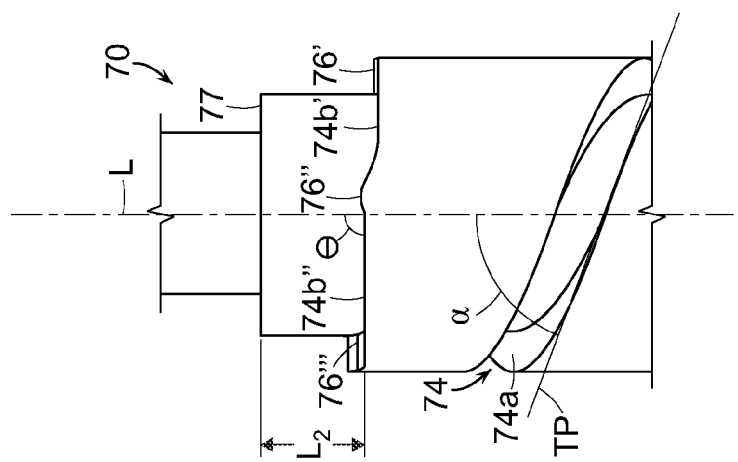
Figure 10A:
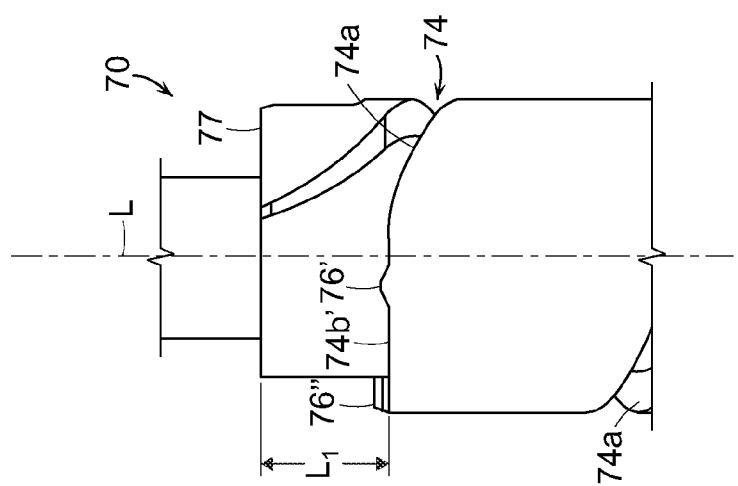
Figure 11C:
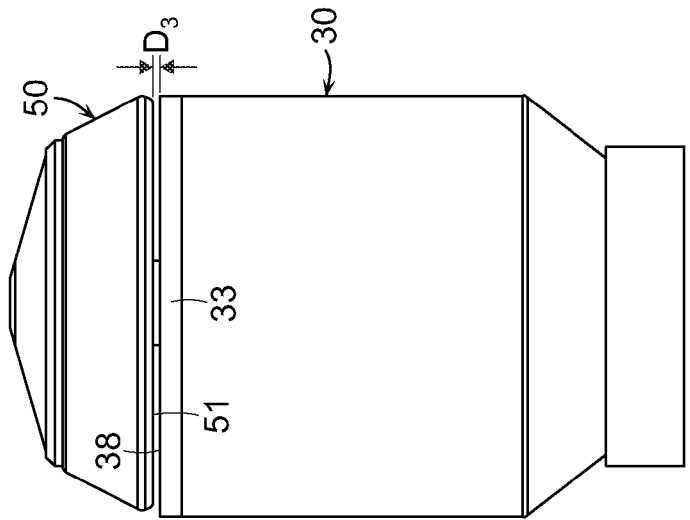
FIGS. 11A-11C are a series of side views of the anvil and the stapling head assembly of the surgical stapler of FIG. 1, each showing a discrete staple forming height correlating with the shaft positions shown in FIGS. 10A-10C, respectively.
Figure 11B:
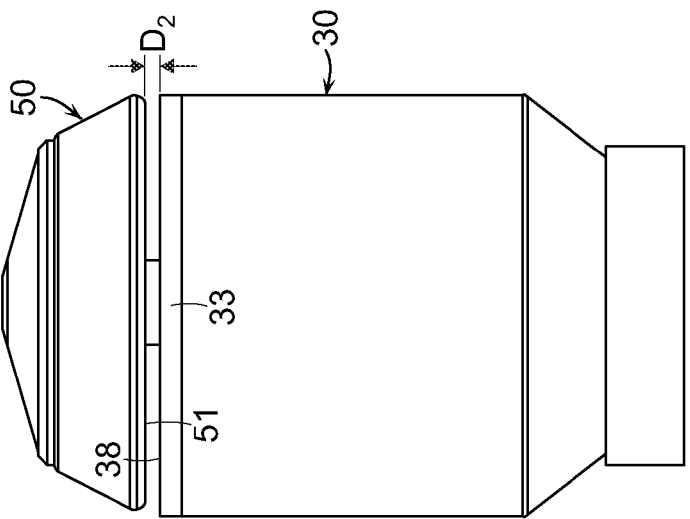
Figure 11A:
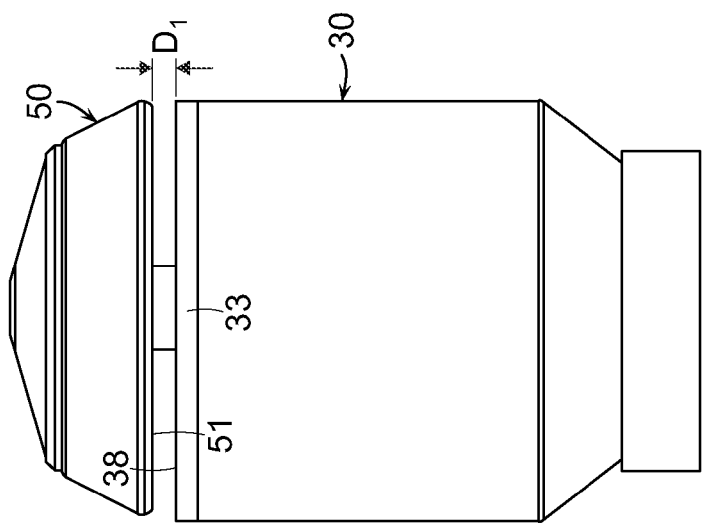

Focusing, now on FIGS. 11A-11C, the stapling head 30 and the anvil 50 are shown in various positions correlating with the dwell portions 74b', 74b'', and 74b''' of the shaft's screw surface. For example, discrete staple forming heights $D_1$, $D_2$, and $D_3$ may be defined between a staple forming surface 51 of anvil 50 and a staple ejection surface 38 of staple cartridge 33. The first height $D_1$ may be greater than the second height $D_2$, which may be greater than the third distance $D_3$, or $D_1 > D_2 > D_3$. Referring collectively to FIGS. 10A-10C and 11A-11C, each dwell portion 74b', 74b'', and/or 74b''' may allow the anvil 50 to be held at the respective staple forming height $D_1$, $D_2$, and/or $D_3$ while the adjustment shaft 70 is being rotated such that the a dwell portion moves along the pin 75 (see FIG. 5). For example, each dwell portion 74b', 74b'', 74b''' may be designed to maintain the anvil's position for a period of shaft rotation of about 60 degrees. In other words, an arc running along each dwell portion's surface may stretch over an angle of approximately 60 degrees.

Figure 9:
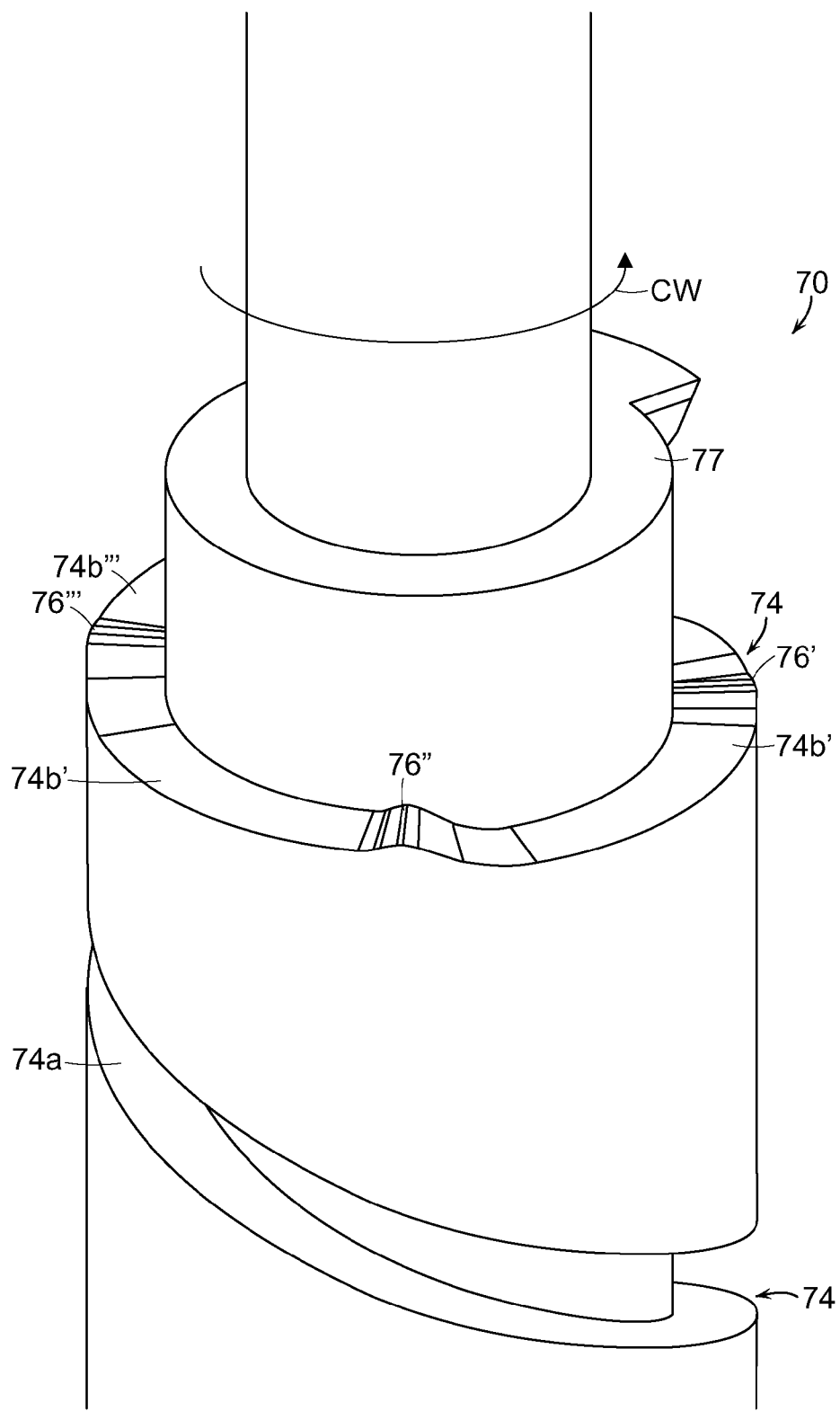
FIG. 9 is a perspective view of a portion of the anvil adjustment shaft of FIG. 8.

Referring to FIGS. 9 and 10A-10C, in various embodiments, at least one transition may separate each dwell portion 74b', 74b", and/or 74b'" to thereby enable the anvil adjustment shaft 70 to be advanced to another position relative to the pin 75 (see FIG. 5). In at least one embodiment, the transition may comprise another ramp portion and/or a partial helical surface. However, in at least one other embodiment, the transition may also comprise at least one delimiter. As can be seen in FIGS. 10A-10C, a first delimiter 76' may separate the screw surface's ramp portion 74a from the first dwell portion 74b', a second delimiter 76" may separate the first dwell portion 74b' from the second dwell portion 74b", and a third delimiter 76'" may separate the second dwell portion 74b" from the third dwell portion 74b'". As mentioned above, each delimiter 76', 76", and/or 76'" may provide tactile feedback to a user while the user rotates the anvil adjustment shaft.

In more detail, referring again to FIGS. 9 and 10A-10C, each delimiter 76', 76", and/or 76'" may comprise a bump or a protrusion in the screw surface. In other words, the screw surface 74 may define a surface topography including the ramp portion 74a and the dwell portions 74b', 74b", and 74b'", and each delimiter 76', 76", and/or 76'" may be an interruption in the surface topography, between the aforementioned portions, respectively. Also, with the exception of the delimiters 76', 76", and/or 76'", the surface topography over any portion of screw surface 74 may be smooth. For example, referring to FIGS. 5, 9, and 10A-10C, the screw surface's ramp portion 74a may include a smooth topography such that the screw surface 74 may move relatively smoothly past the pin 75 when the anvil adjustment shaft 70 is rotated with respect to body 10. However, when the pin 75 reaches the end of the ramp portion 74a, the surface topography may be interrupted by the first delimiter 76'. Accordingly, as the screw surface 74 is advanced over pin 75, the adjustment shaft 70, which may be extending proximally from body 10 in a smooth fashion as shaft 70 is being rotated, may jump, push, or pull in an abrupt or discontinuous fashion, or otherwise provide tactile feedback to a user, as the first delimiter 76' contacts the pin 75, owing to the interruption in the surface topography of the screw surface 74 at the delimiter 76'. The action of the first delimiter 76' passing over the pin 75 may provide a user rotating the shaft 70 with an indication that the first discrete staple forming height $D_1$ (see FIG. 11A) has been reached as the pin 75 is now received at the first dwell portion 74b'. Continued rotation of shaft 70 for the dwell period, which, as mentioned above, may be approximately 60 degrees, may not adjust the first staple forming height $D_1$. Accordingly, the user does not necessarily need to focus on the exact rotational position at which anvil adjustment shaft 70 is located, as long as the user knows that the first staple forming height $D_1$ will not change until the shaft 70 is further rotated to bring another delimiter into contact with the pin 75. Further, the user may rotate the anvil adjustment shaft 70 back and forth such that the pin 75 is relatively moved along first dwell portion 74b', between first delimiter 76' and second delimiter 76". As the delimiters protrude from the surface of first dwell portion 74b', the user, through the anvil adjustment shaft 70, may feel when the pin 75 contacts the first or second delimiter 76', 76" at the respective ends of first dwell portion 74b', thereby providing confidence to the user that the first staple forming height $D_1$ has been reached.

Referring to FIGS. 5, 9, and 10A-10C, if the user desires to change the staple forming height from the first staple forming height $D_1$ to the second staple forming height $D_2$ (see FIGS. 11A-11B), the user may further rotate the anvil adjustment shaft 70 such that the second delimiter 76" contacts the pin 75. When the pin 75 reaches the end of the first dwell portion 74b', the surface topography may be interrupted by the second delimiter 76". Accordingly, as the screw surface 74 is advanced over pin 75, the adjustment shaft 70, which may be rotating smoothly while the pin 75 is contacting the first dwell portion 74b', may jump, push, or pull in an abrupt or discontinuous fashion, or otherwise provide tactile feedback to a user, as the second delimiter 76" contacts the pin 75 owing to the interruption in the surface topography of the screw surface 74 at the delimiter 76'". The action of the second delimiter 76" passing over the pin 75 may provide a user rotating the shaft 70 with an indication that the second discrete staple forming height $D_2$ (see FIG. 11B) has been reached as the pin 75 is now received at the second dwell portion 74b". Continued rotation of shaft 70 for the dwell period, which, as mentioned above, may be approximately 60 degrees, may not adjust the second staple forming height $D_2$. Accordingly, the user does not necessarily need to focus on the exact rotational position at which anvil adjustment shaft 70 is located, as long as the user knows that the second staple forming height $D_2$ will not change until the shaft 70 is further rotated to bring another delimiter into contact with the pin 75. Further, the user may rotate the anvil adjustment shaft 70 back and forth such that the pin 75 is relatively moved along second dwell portion 74b", between second delimiter 76" and third delimiter 76'". As the delimiters protrude from the surface of second dwell portion 74b", the user, through the anvil adjustment shaft 70, may feel when the pin 75 contacts the second or third delimiter 76", 76'" at the respective ends of second dwell portion 74b", thereby providing confidence to the user that the second staple forming height $D_2$ has been reached.

Similarly, referring still to FIGS. 5, 9, and 10A-10C, if the user desires to change the staple forming height from the second staple forming height $D_2$ to the third staple forming height $D_3$ (see FIGS. 11B-11C), the user may further rotate the anvil adjustment shaft 70 such that the third delimiter 76'" contacts the pin 75. When the pin 75 reaches the end of the second dwell portion 74b", the surface topography may be interrupted by the third delimiter 76'". Accordingly, as the screw surface 74 is advanced over pin 75, the adjustment shaft 70, which may be rotating smoothly while the pin 75 is contacting the second dwell portion 74b", may jump, push, or pull in an abrupt or discontinuous fashion, or otherwise provide tactile feedback to a user, as the third delimiter 76'" contacts the pin 75, owing to the interruption in the surface topography of the screw surface 74 at the delimiter 76'". The action of the third delimiter 76'" passing over the pin 75 may provide a user rotating the shaft 70 with an indication that the third discrete staple forming height $D_3$ (see FIG. 11C) has been reached as the pin 75 is now received at the third dwell portion 74b'". Continued rotation of shaft 70 for the dwell period, which, as mentioned above, may be approximately 60 degrees, may not adjust the third staple forming height $D_3$. Accordingly, the user does not necessarily need to focus on the exact rotational position at which anvil adjustment shaft 70 is located, as long as the user knows that the third staple forming height $D_3$ will not change until the shaft 70 is further rotated to bring a stop 78 into contact with the pin 75, thereby preventing further movement of the pin 75 relative to the screw surface 74, towards stop 78. The stop 78 may be a wall formed at the end of the third delimiter portion 74b'". Further, the user may rotate the anvil adjustment shaft 70 back and forth such that the pin 75 is relatively moved along third dwell portion 74b'", between third delimiter 76'" and stop 78. As the stop and delimiter 76'" protrude from the surface of third dwell portion 74b", the user, through the anvil adjustment shaft 70, may feel when the pin 75 contacts the third delimiter 76''' or stop 78 at the respective ends of third dwell portion 74b''', thereby providing confidence to the user that the third staple forming height $D_3$ has been reached.

Figure 15:
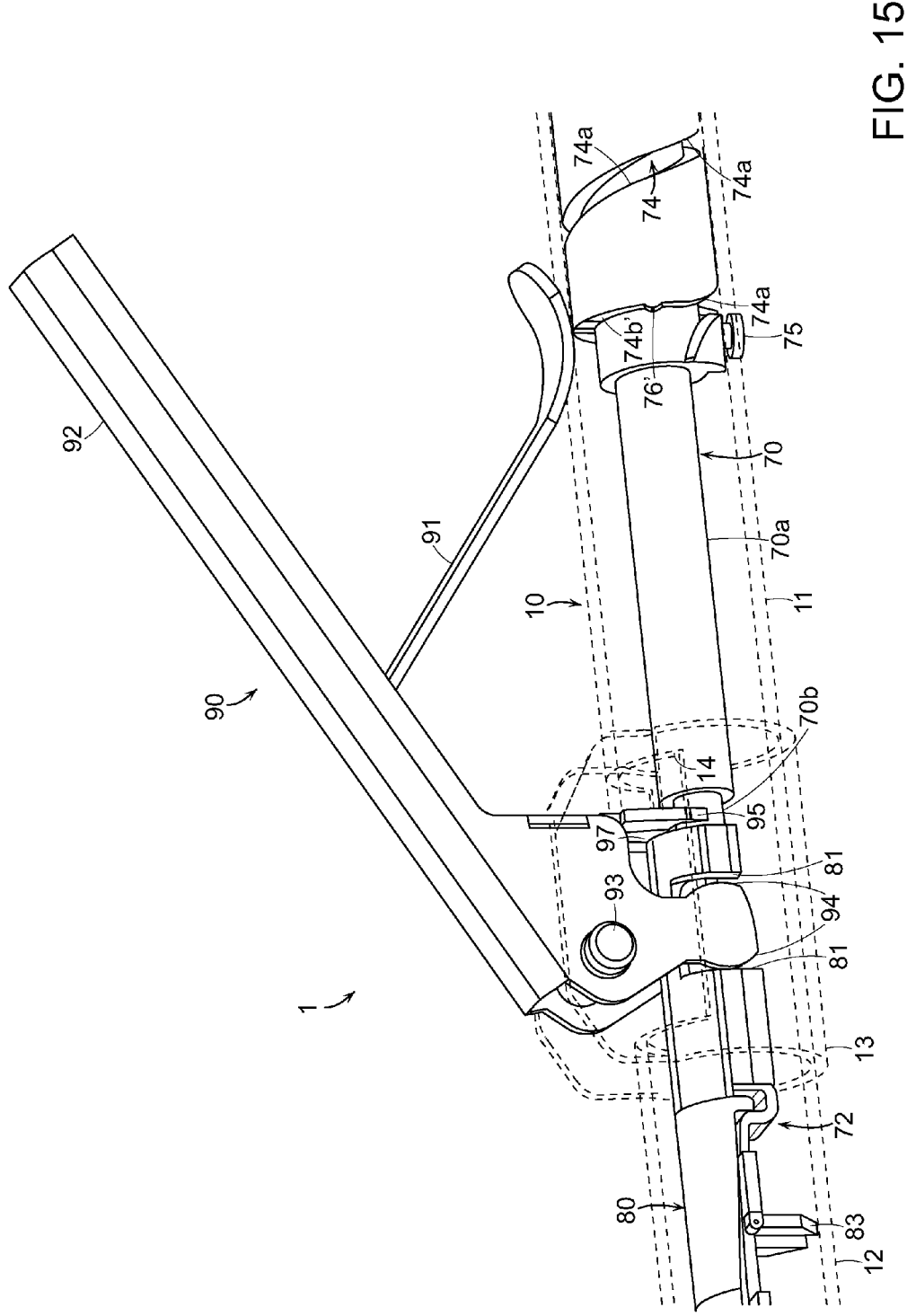
FIG. 15 is a front perspective view of a portion of the surgical stapler of FIG. 3, showing the trigger and lockout stem interfacing with a drive band and the adjustment shaft, respectively.

In various embodiments, referring to FIGS. 9 and 15, for example, the screw surface 74 may be closed over the ramp portion 74a and open over the dwell portions 74b', 74b'', 74b'''. In other words, the screw surface's ramp portion may include proximal and distal walls whereas the screw surface's dwell portions may only include proximal walls. In use, the pin 75 may be biased against the dwell portions due to tissue being clamped between anvil 50 and stapling head 30 when the anvil 50 is at an appropriate staple forming height from the head 30, as discussed above (see FIGS. 11A-11C).

While at least one embodiment described above show the delimiters 76', 76'', and/or 76''' as being formed as bumps or protrusions in the screw surface 74, the delimiters may also take the form of indentations in the screw surface. Also, the delimiters may be a separate piece from the adjustment shaft 70 such that they may be attached thereto. In any event, the delimiters may provide tactile feedback to a user as the user rotates the shaft 70. Further, while a delimiter is shown as separating the ramp portion 74a from the first dwell portion 74b', and so on, the screw surface may not include a dwell portion or dwell portions. In such embodiments, the screw surface may comprise multiple ramp portions separated, at desired intervals, by at least one delimiter. Accordingly, a user may be informed, via tactile feedback, when an appropriate staple forming height, between the anvil 50 and staple cartridge 33 (see, e.g., FIG. 11A) has been obtained.

Figure 12:
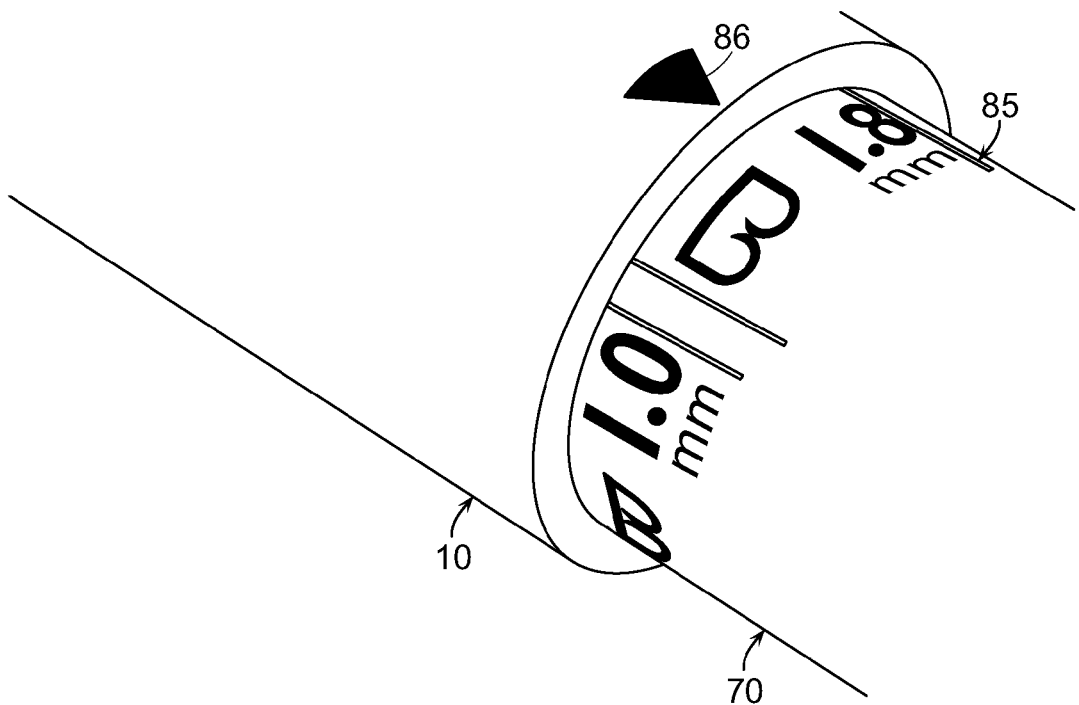
FIG. 12 illustrates a non-limiting embodiment a portion of an anvil adjustment shaft including reference indicia.
Figure 13:
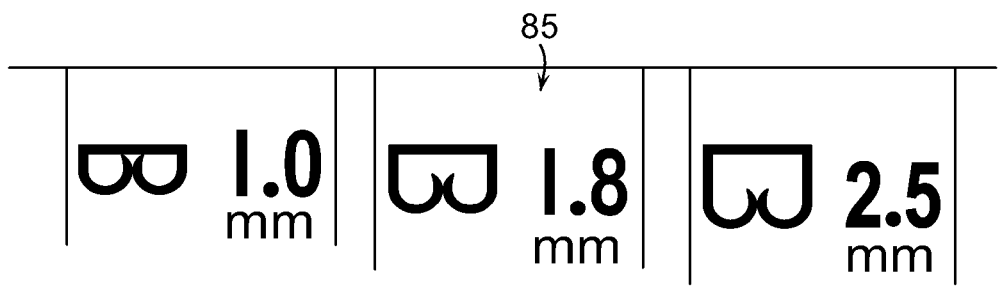
FIG. 13 illustrates three reference indicia from the portion of the adjustment shaft of FIG. 12.

In addition to tactile feedback, the surgical stapler 1 may include visual reference indicia to provide a user with an indication of when the aforementioned staple forming height(s) have been reached. For example, referring now to FIGS. 12-13, the anvil adjustment shaft 70 may include reference indicia 85 printed or formed in the shaft's surface that, via a marking 86 on body 10, to provide an indication of when a discrete staple forming height, such as $D_1, D_2, D_3$ (see FIGS. 11A-11C), has been reached. In at least one embodiment, the respective staple forming heights may be 2.5 mm, 1.8 mm, and 1.0 mm, and the reference indicia 85 may indicate the same. In any event, the incorporation of visual indicia, delimiters, and/or dwell portions, as discussed above, into the anvil adjustment shaft 70 may remove the need for a staple height indicator mechanism separate from the shaft.

Additionally, while at least one embodiment described above has illustrated the screw surface 74 as being defined by a channel formed in anvil adjustment shaft 70, the screw surface may, in at least one embodiment, alternatively be defined by a thread projecting from the anvil adjustment shaft 70. In such embodiments, pin 75 may be employed or another thread mating component may be used to engage the screw surface, such as a fork projecting from the inside of body 10.

Further, while the screw surface 74 discussed above is described as being a part of anvil adjustment shaft 70, it is to be understood that such screw surface could alternatively be a part of the body 10. In such embodiments, an engagement portion, such as a pin or other thread engaging component, would likewise be fixed to the adjustment shaft 70 instead of to the body 10. In any event, rotation of the shaft 70 may cause a screw surface to rotate with respect to an engagement portion such that the shaft 70 and, hence, the anvil 50 translate with respect to the body 10 and/or stapling head 30.

Figure 14:
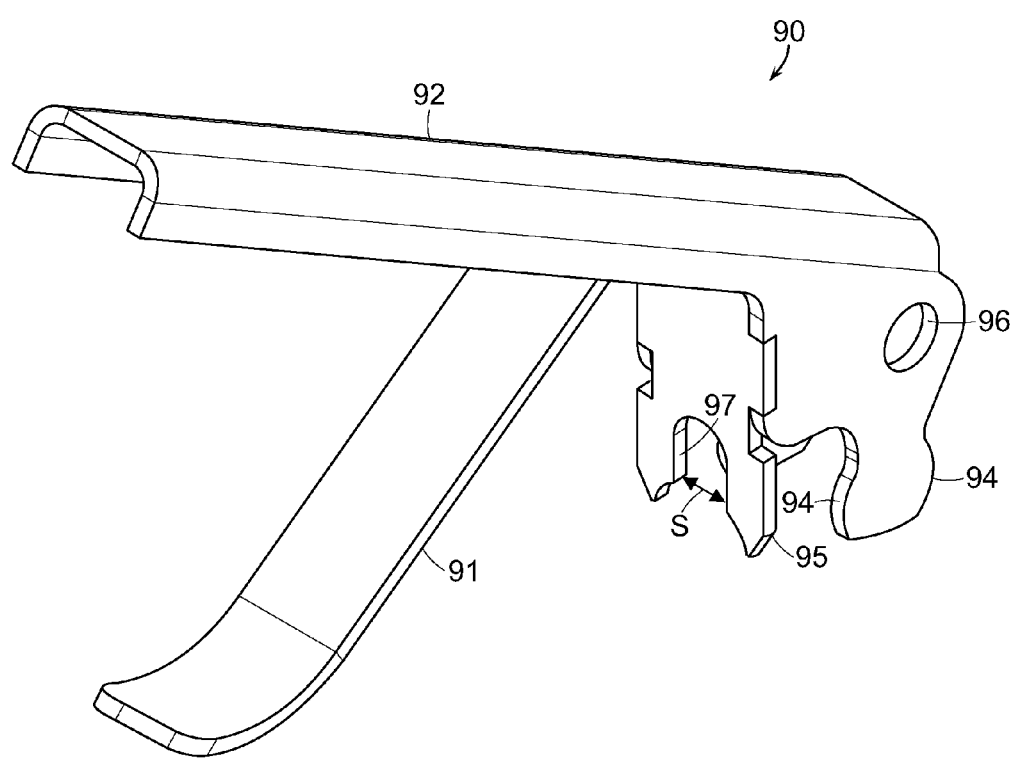
FIG. 14 is a rear perspective view of a trigger of the surgical stapler of FIG. 1; the trigger includes a lockout stem.

In various embodiments, as mentioned above and referring to FIG. 5, before the anvil 50 is at an appropriate distance from staple cartridge 33, the trigger 90 may cooperate with the adjustment shaft 70 to prevent the trigger 90 from moving substantially towards body 10 or otherwise causing staple drivers 34 and/or cutting member 32 to be actuated, thereby preventing the unintended firing of the surgical stapler 1. In other words, the trigger may include a lockout. For example, in at least one embodiment and referring to FIG. 8, the actuation shaft 70 may comprise the first, proximal portion 70a defining a first width $W_1$, and the second, distal portion 70b defining a second width $W_2$. Further, referring to FIG. 14, the trigger 90 may comprise lockout stem 95 extending from lever 92, the stem 95 defining an opening 97 having a size S. The lockout stem may resemble a fork with two tines, or a yoke. In any event, the size S of the opening 97 may be smaller than the first width $W_1$ of the proximal portion 70a but the size S of the opening 97 may be larger than or equal to the second width $W_2$ of the distal portion 70b, or $W_1 > S \geq W_2$.

Referring now to FIG. 15, the lockout stem 95 may be positioned through body opening 14 such that the stem 95 is operable to engage either the shaft's proximal portion 70a or the shaft's distal portion 70b. If the lockout stem 95 is longitudinally positioned over the proximal portion 70a, the trigger lever 92 may be prevented from moving substantially towards body 10 due to interference between the lockout stem 95 and the shaft's proximal portion 70a. In other words, because the proximal portion's width $W_1$ (see FIG. 8) is larger than the size S of the lockout stem's opening 97 (see FIG. 14), the trigger lever 92 may be prevented from causing the drive band 80 to actuate, as described above, thereby preventing inadvertent firing of staples 31 and/or cutting member 32 (see FIG. 3). However, if the lockout stem 95 is longitudinally positioned over the distal portion 70b, the trigger lever 92 may be allowed to move substantially towards body 10 due to a lack of interference between the lockout stem 95 and the shaft's distal portion 70b. In other words, because the distal portion's width $W_2$ (see FIG. 8) is smaller than or equal to the size S of the lockout stem's opening 97 (see FIG. 14), the trigger lever 92 may be allowed to move and cause the drive band 80 to actuate, as described above, thereby firing staples 31 and/or cutting member 32 (see FIG. 3). In such embodiments, the opening 97 may receive the shaft's distal portion 70b and allow the lever 92 to move towards body 10 until the distal portion 70b reaches the end of opening 97.

Further, referring to FIG. 15, the shaft's distal portion 70b may be positioned along anvil adjustment shaft 70 such that the distal portion 70b correlates with an appropriate staple forming height. For example, the distal portion 70b may be axially positioned along shaft 70 such that the lockout stem 95 is longitudinally positioned over the distal portion 70b when the pin 75 is received in a dwell portion, such as first dwell portion 74b'. Accordingly, the lockout stem 95 may only allow the staple drivers 34 and/or cutting member 32 (see FIG. 3) to be fired when a desired staple forming height has been reached, without the need for a lockout lever or mechanism separate from the trigger 90. Further, referring to FIG. 14, the lockout stem 95 may be unitary and integrally formed from the same piece of material as trigger spring 91. However, in at least one embodiment, the lockout stem 95, trigger spring 91, and lever 92 may be unitary and integrally formed from the same piece of material.

In various embodiments, and as mentioned above, the surgical stapler may be straight instead of curved, as described above. Accordingly, referring now to FIG. 16, a surgical stapler 101 is shown. Surgical stapler 101 may include a body 110, a stapling head 130, an anvil 150, an anvil adjustment shaft 170, and a trigger 190, similar to that described above. However, shaft portion 112 of body 110 may be straight. Further, the stapling head 130 and anvil 150 may be linear and project axially away from the body 110. It should be noted that, referring to the surgical staplers 1 and 101 depicted in FIGS. 1 and 16, respectively, because each stapling head 30, 130 may be removed from the surgical stapler's body 10, 110 as discussed above, the stapling heads 30, 130 and anvils 50, 150 may be interchanged with each other, for example. Further, other stapling head and anvil configurations may be employed in addition to the above describe heads 30, 130 and anvils 50, 150.

Figure 16:
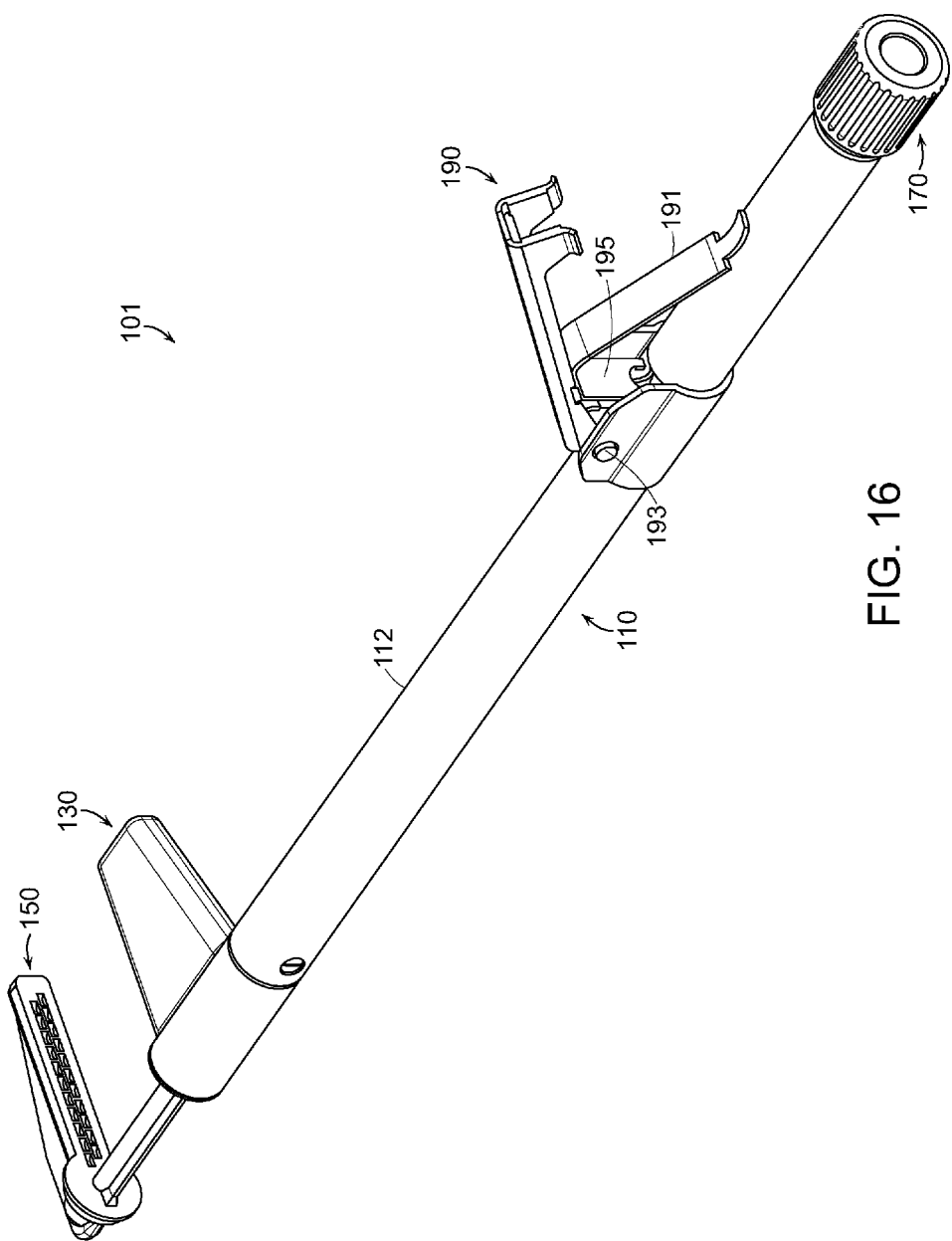
FIG. 16 is a perspective view of a non-limiting embodiment of a surgical stapler including a straight shaft portion.

Also, referring now to FIG. 17, the anvil adjustment shaft 170 and trocar 173 may be unitary and integrally formed from the same piece of material. Thus, the shaft's distal portion 170b may project from the proximal portion 170a and abut the trocar 173. Further, referring to FIG. 18, a drive bar 180 is shown. Drive bar may allow movement of trigger 190 (see FIG. 16) to actuate drive bar 180 towards stapling head 130 to eject staples and/or actuate a cutting member (not shown) therefrom. Briefly, the drive bar may be elongate and generally tubular in shape and include proximal drive surfaces 181 and distal drive surfaces 182. Referring to FIGS. 16 and 18, the proximal drive surfaces 181 may be configured to receive driving motions from trigger 190 and the distal drive surfaces 182 may be configured to engage staple drivers and/or a cutting member (not shown) within stapling head 130, as described above. Also, the drive bar 180 may include a passage 187 adapted to receive anvil adjustment shaft 170 (see FIG. 17) therethrough. In at least one embodiment, the stapler 101 may not include a cutting member, and may primarily function to staple or seal, but not transect, tissue.

It should be appreciated that the straight stapler 101 and the curved stapler 1, discussed above (see FIGS. 16 and 1, respectively) may contain significantly fewer components than similar current surgical staplers available on the market. For example, referring to straight surgical stapler 101, and in particular to anvil adjustment shaft, the combination of a knob 179, with a closure screw or screw surface 174, and trocar 173 into one integral component, anvil adjustment shaft 170, reduces part count of a surgical stapler. Further reducing component count may be obtained by combining a ramp portion 174a with a dwell portion 174b into screw surface 174. As discussed above, the screw surface's ramp portion 174a may allow initial, course axial movement of shaft 170 with respect to body 110, and the dwell portion(s) 174b may establish at least one discrete, predetermined staple forming height between anvil 150 and stapling heard 130. Overall, ignoring the anvil and stapling head components, the surgical stapler 101 may include only seven components compared to over thirty in current devices. Referring to FIGS. 16-18, the seven components may include the body 110, the firing trigger 190, a hinge pin 193 pivotally coupling the trigger 190 to the body 110, a trigger spring 191 integrally formed with a lockout stem 195, the anvil adjustment shaft 170, a screw pin (not shown, see screw pin 75 seen in FIG. 3, for example) operably engaging the shaft's screw surface 174, and the drive bar 180. Additionally, the part count may be further reduced. For example, the hinge pin 193 may be eliminated by combining a hinge detent or flexible tab, for example, into the trigger 190 itself. Further, spring 191 and lockout stem 195 may also be integrally formed with the trigger 190. Also, the screw pin (not shown) may be eliminated by incorporating a protrusion extending from an inner surface of body 110 such that the screw protrusion may engage the screw surface 174. In any event, the aforementioned components of surgical stapler 101 may provide similar functionality as that described above. This simplified stapler architecture using only a few manufacturing techniques may be broadly applicable, and should be appropriate for a multi-use, sterilizable device, that costs significantly less and requires less manufacturing time than similar, currently available surgical staplers. Accordingly, in at least one embodiment, a stapler, including the above-mentioned components, less the anvil and stapling head parts, may be provided that is reusable. Also, in at least one embodiment, the anvil and/or stapling head, including a staple cartridge, may further be disposable.

In at least one exemplary experiment, the aforementioned minimization of part count was accomplished by comparing each component to a part criteria list to see if that part was needed. The only ones remaining were those listed above and required for assembly reasons, possessed unique material properties, or which moved with respect to other parts in the stapler.

While the embodiments have been described, it should be apparent, however, that various modifications, alterations and adaptations to the embodiments may occur to persons skilled in the art with the attainment of some or all of the advantages of the various embodiments. For example, according to various embodiments, a single component or step may be replaced by multiple components or steps, and multiple components or steps may be replaced by a single component or step, to perform a given function or functions or accomplish a given objective. Further, the various components described above may be made from a variety of materials. For example, the components may be made from any combination of metal, plastic, and/or a biocompatible material. Moreover, various components, such as the trigger, drive band, and anvil adjustment band may be made and bent or folded from sheet metal. This application is therefore intended to cover all such modifications, alterations and adaptations without departing from the scope and spirit of the appended claims.

The devices disclosed herein can be designed to be disposed of after a single use, or they can be designed to be used multiple times. In either case, however, the devices can be reconditioned for reuse after at least one use. Reconditioning can include a combination of the steps of disassembly of the device, followed by cleaning or replacement of particular pieces, and subsequent reassembly. In particular, the devices can be disassembled, and any number of particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

The devices described herein may be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapler, comprising:
   a body comprising:
      a handle portion; and
      a shaft portion extending from the handle portion;
   a stapling head assembly releasably coupled to the shaft portion, the stapling head assembly comprising:
      a staple cartridge for supporting one or more surgical staples; and
      at least one staple driver for engaging and driving the staples from the staple cartridge;
   a drive system for applying drive motions to the staple driver;
   an anvil movably supported relative to the staple cartridge for axial movement toward and away from the staple cartridge; and
   an anvil adjustment assembly for selectively adjusting an axial position of the anvil relative to the staple cartridge, wherein the anvil adjustment assembly comprises an adjustment shaft and a trocar coupled to the adjustment shaft for travel therewith, the trocar configured for removable attachment to the anvil, wherein one of the adjustment shaft or the body comprises an engagement portion, and wherein the other of the adjustment shaft or the body comprises:
      a screw surface comprising at least one ramp portion, at least one dwell portion, and at least one delimiter separating the at least one dwell portion from the at least one ramp portion, the at least one ramp portion wherein the at least one delimiter comprises at least one of a bump, a protrusion, or a notch configured to operably engage the engagement portion to cause the adjustment shaft to move relative to the body when the adjustment shaft is rotated.

2. The surgical stapler of claim 1, further comprising a trigger movably coupled to the body, the trigger configured to actuate the drive system when the trigger is moved, wherein the adjustment shaft comprises a first portion defining a first width and a second portion defining a second width, wherein the trigger further comprises a lockout stem defining an opening having a size, wherein the size of the opening is smaller than the first width but the opening is larger than or equal to the second width.

3. The surgical stapler of claim 1, wherein the screw surface defines a surface topography, and wherein the at least one delimiter is an interruption in the surface topography.

4. The surgical stapler of claim 1 wherein the adjustment shaft comprises an adjustment shaft axis, wherein the at least one ramp portion slopes at an angle of less than 90 degrees relative to the adjustment shaft axis and the at least one dwell portion is substantially perpendicular to the adjustment shaft axis.

5. The surgical stapler of claim 1, further comprising visual indicia on the anvil adjustment shaft correlating with the at least one dwell portion.

6. A surgical stapler, comprising:
   a body;
   a stapling head operably coupled to the body;
   an anvil movably supported relative to the stapling head for selective travel toward and away from the stapling head; and
   an anvil adjustment shaft supported by the body for selectively adjusting a position of the anvil relative to the stapling head, wherein one of the adjustment shaft or the body comprises an engagement portion, and wherein the other of the adjustment shaft or the body comprises:
      a screw surface comprising a first portion and a second portion, the first portion configured to operably engage the engagement portion to cause the adjustment shaft to move relative to the body when the adjustment shaft is rotated; and
      at least one delimiter separating the first portion from the second portion wherein the at least one delimiter comprises at least one of a bump, a protrusion, or a notch.

7. The surgical stapler of claim 6, wherein the screw surface defines a surface topography, and wherein the at least one delimiter is an interruption in the surface topography.

8. The surgical stapler of claim 6 wherein the adjustment shaft comprises an adjustment shaft axis, wherein the first portion slopes at an angle of less than 90 degrees relative to the adjustment shaft axis and the second portion is substantially perpendicular to the adjustment shaft axis.

9. The surgical stapler of claim 6, further comprising a drive system configured to eject staples from the stapling head and a trigger movably coupled to the body, the trigger configured to actuate the drive system when the trigger is moved, wherein the adjustment shaft comprises a first portion defining a first width and a second portion defining a second width, wherein the trigger further comprises a lockout stem defining an opening having a size, wherein the size of the opening is smaller than the first width but the opening is larger than or equal to the second width.

10. A surgical stapler, comprising:
    a body;
    a stapling head operably coupled to the body;
    an anvil movably supported relative to the stapling head for selective travel toward and away from the stapling head; and
    an anvil adjustment shaft supported by the body for selectively adjusting a position of the anvil relative to the stapling head, wherein one of the adjustment shaft or the body comprises an engagement portion, and wherein the other of the adjustment shaft or the body comprises:
       a screw surface comprising at least one ramp a first dwell and a second dwell, the at least one ramp portion configured to operably engage the engagement portion to cause the adjustment shaft to move relative to the body when the adjustment shaft is rotated; a first tactile feedback delimiter positioned intermediate the at least one ramp and the first dwell; and a second tactile feedback delimiter positioned intermediate the first dwell and the second dwell.

11. The surgical stapler of claim 10, wherein the adjustment shaft comprises an adjustment shaft axis, wherein the at least one ramp portion slopes at an angle of less than 90 degrees relative to the adjustment shaft axis, wherein the first dwell is substantially perpendicular to the adjustment shaft axis, and wherein the second dwell is substantially perpendicular to the adjustment shaft axis.

12. The surgical stapler of claim 10, wherein the first tactile feedback delimiter and the second tactile feedback delimiter are bumps.

13. The surgical stapler of claim 10, wherein the first tactile feedback delimiter and the second tactile feedback delimiter are protrusions.

14. The surgical stapler of claim 10, wherein the screw surface defines a surface topography, and wherein the first tactile feedback delimiter and the second tactile feedback delimiter each comprise an interruption in the surface topography.

15. The surgical stapler of a drive system configured to eject staples from the stapling head and was inserted a trigger movably coupled to the body, the trigger configured to actuate the drive system when the trigger is moved, wherein the adjustment shaft comprises a first portion defining a first width and a second portion defining a second width, wherein the trigger further comprises a lockout stem defining an opening having a size, wherein the size of the opening is smaller than the first width but the opening is larger than or equal to the second width.

16. A surgical stapler, comprising:
a body comprising:
    a handle portion; and
    a shaft portion extending from the handle portion;
a stapling head assembly comprising:
    a staple cartridge portion; and
    an anvil movably supported relative to the staple cartridge portion for axial movement toward and away from the staple cartridge portion; and
an anvil adjustment assembly for selectively adjusting an axial position of the anvil relative to the staple cartridge portion, wherein the anvil adjustment assembly comprises an adjustment shaft and a trocar, wherein the trocar is coupled to the adjustment shaft for travel therewith, wherein the trocar is configured for removable attachment to the anvil, wherein one of the adjustment shaft or the body comprises an engagement portion, and wherein the other of the adjustment shaft or the body comprises:
    a screw surface comprising a ramp portion, a dwell portion, and at least one delimiter separating the dwell portion from the ramp portion, wherein the at least one delimiter comprises at least one of a bump, a protrusion, and a notch, and wherein the ramp portion is configured to operably engage the engagement portion to cause the adjustment shaft to move relative to the body when the adjustment shaft is rotated.

17. The surgical stapler of claim 16, further comprising:
a drive system configured to deploy staples from the staple cartridge portion; and
a trigger movably coupled to the body, wherein the trigger is configured to actuate the drive system when the trigger is moved, wherein the adjustment shaft comprises a first portion defining a first width and a second portion defining a second width, wherein the trigger further comprises a lockout stem defining an opening having a size, wherein the size of the opening is smaller than the first width and wherein the size of the opening is larger than or equal to the second width.

18. The surgical stapler of claim 16, wherein the screw surface defines a surface topography, and wherein the at least one delimiter is an interruption in the surface topography.

19. The surgical stapler of claim 16, wherein the adjustment shaft comprises an adjustment shaft axis, wherein the ramp portion slopes at an angle of less than 90 degrees relative to the adjustment shaft axis, and wherein the dwell portion is substantially perpendicular to the adjustment shaft axis.

20. The surgical stapler of claim 16, further comprising visual indicia on the anvil adjustment shaft correlating with the dwell portion.

21. A surgical stapler, comprising:
a body;
a stapling head operably coupled to the body; and
an adjustment shaft supported by the body for selectively adjusting a position of an anvil relative to the stapling head, wherein one of the adjustment shaft or the body comprises an engagement portion, and wherein the other of the adjustment shaft or the body comprises:
    a screw surface comprising at least one ramp, a first dwell, and a second dwell, the at least one ramp configured to operably engage the engagement portion to cause the adjustment shaft to move relative to the body when the adjustment shaft is rotated;
    a first tactile feedback delimiter positioned relative to the first dwell; and
    a second tactile feedback delimiter positioned relative to the second dwell.

22. The surgical stapler of claim 21, wherein the adjustment shaft comprises an adjustment shaft axis, wherein the at least one ramp slopes at an angle of less than 90 degrees relative to the adjustment shaft axis, wherein the first dwell is substantially perpendicular to the adjustment shaft axis, and wherein the second dwell is substantially perpendicular to the adjustment shaft axis.

23. The surgical stapler of claim 21, wherein the first tactile feedback delimiter and the second tactile feedback delimiter are bumps.

24. The surgical stapler of claim 21, wherein the first tactile feedback delimiter and the second tactile feedback delimiter are protrusions.

25. The surgical stapler of claim 21, wherein the screw surface defines a surface topography, and wherein the first tactile feedback delimiter and the second tactile feedback delimiter each comprise an interruption in the surface topography.

26. The surgical stapler of claim 21, further comprising a drive system configured to eject staples from the stapling head and a trigger movably coupled to the body, wherein the trigger is configured to actuate the drive system when the trigger is moved, wherein the adjustment shaft comprises a first portion defining a first width and a second portion defining a second width, wherein the trigger further comprises a lockout stem defining an opening having a size, wherein the size of the opening is smaller than the first width, and wherein the size of the opening is larger than or equal to the second width.

27. A surgical stapler, comprising:
a body comprising:
    a handle portion; and
    a shaft portion extending from the handle portion;
a stapling head assembly comprising:
    a first portion; and
    a second portion movably supported relative to the first portion for axial movement toward and away from the first portion; and
an adjustment assembly for selectively adjusting an axial position of the second portion relative to the first portion, wherein the adjustment assembly comprises an adjustment shaft, wherein one of the adjustment shaft or the body comprises an engagement portion, and wherein the other of the adjustment shaft or the body comprises:
    a screw surface comprising at least one ramp portion, at least one dwell portion, and at least one delimiter separating the at least one dwell portion from the at least one ramp portion, wherein the at least one delimiter comprises at least one of a bump, a protrusion, and a notch, and wherein the at least one ramp portion is configured to operably engage the engagement portion to cause the adjustment shaft to move relative to the body when the adjustment shaft is rotated.

28. The surgical stapler of claim 6 wherein the stapling head comprises a staple cartridge.

29. The surgical stapler of claim 10 wherein the stapling head comprises a staple cartridge.

30. The surgical stapler of claim 16 wherein the staple cartridge portion comprises a staple cartridge.

31. The surgical stapler of claim 21 wherein the stapling head comprises a staple cartridge.

32. The surgical stapler of claim 27 wherein one of the first and second portions of the stapling head assembly comprises a staple cartridge.

* * * * *